(12) United States Patent
Klomann et al.

(10) Patent No.: US 10,738,215 B2
(45) Date of Patent: Aug. 11, 2020

(54) MONOBLOC AEROSOL TUBE OR CAN HAVING A COATING COMPOSITION

(71) Applicant: PPG Industries Ohio, Inc., Cleveland, OH (US)

(72) Inventors: Sabine Klomann, Ruetlingen (DE); Anthony M. Chasser, Greensburg, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 101 days.

(21) Appl. No.: 16/069,561

(22) PCT Filed: Jan. 13, 2017

(86) PCT No.: PCT/EP2017/050724
§ 371 (c)(1),
(2) Date: Jul. 12, 2018

(87) PCT Pub. No.: WO2017/121879
PCT Pub. Date: Jul. 20, 2017

(65) Prior Publication Data
US 2019/0023939 A1 Jan. 24, 2019

Related U.S. Application Data

(63) Continuation of application No. 15/151,547, filed on May 11, 2016, now abandoned, and a continuation of
(Continued)

(30) Foreign Application Priority Data

Jan. 15, 2016 (EP) ...................... 16151619
Jan. 15, 2016 (EP) ...................... 16151620
Jan. 15, 2016 (EP) ...................... 16151621

(51) Int. Cl.
| | | |
|---|---|---|
| *C09D 175/12* | (2006.01) | |
| *C09D 5/02* | (2006.01) | |
| *C09D 5/03* | (2006.01) | |
| *B27N 7/00* | (2006.01) | |
| *C08G 18/48* | (2006.01) | |
| *C08G 18/66* | (2006.01) | |
| *C08G 18/67* | (2006.01) | |
| *C08G 18/75* | (2006.01) | |
| *C08G 18/79* | (2006.01) | |
| *C08G 18/80* | (2006.01) | |
| *C08G 18/24* | (2006.01) | |
| *C09D 175/16* | (2006.01) | |
| *C08G 18/32* | (2006.01) | |
| *C08G 18/34* | (2006.01) | |
| *C09D 175/02* | (2006.01) | |
| *B65D 1/12* | (2006.01) | |
| *C07C 275/14* | (2006.01) | |
| *C07C 275/26* | (2006.01) | |

(Continued)

(52) U.S. Cl.
CPC ........... *C09D 175/12* (2013.01); *B27N 7/005* (2013.01); *B65D 1/12* (2013.01); *C07C 275/14* (2013.01); *C07C 275/26* (2013.01); *C08G 18/246* (2013.01); *C08G 18/3275* (2013.01); *C08G 18/348* (2013.01); *C08G 18/48* (2013.01); *C08G 18/4854* (2013.01); *C08G 18/6692* (2013.01); *C08G 18/672* (2013.01); *C08G 18/73* (2013.01); *C08G 18/751* (2013.01); *C08G 18/755* (2013.01); *C08G 18/792* (2013.01); *C08G 18/8041* (2013.01); *C09D 5/02* (2013.01); *C09D 5/03* (2013.01); *C09D 175/02* (2013.01); *C09D 175/16* (2013.01); *B27N 3/002* (2013.01)

(58) Field of Classification Search
CPC .......... C09D 175/12; C09D 5/02; C09D 5/03; C09D 175/16; C09D 175/02; B27N 7/005; B27N 3/002; C08G 18/4854; C08G 18/6692; C08G 18/672; C08G 18/755; C08G 18/792; C08G 18/8041; C08G 18/246; C08G 18/3275; C08G 18/348; C08G 18/73; C08G 18/751; C08G 18/48; C07C 275/14; C07C 275/26; B65D 1/12

See application file for complete search history.

(56) References Cited

U.S. PATENT DOCUMENTS

| | | |
|---|---|---|
| 3,294,751 A | 12/1966 | Beitchman |
| 3,420,787 A | 1/1969 | Reymore et al. |

(Continued)

FOREIGN PATENT DOCUMENTS

| | | |
|---|---|---|
| CN | 1662618 A | 8/2005 |
| CN | 101098935 A | 1/2008 |

(Continued)

OTHER PUBLICATIONS

Machine English translation of CN101098935.
(Continued)

*Primary Examiner* — Michael C Miggins
(74) *Attorney, Agent, or Firm* — Diane R. Meyers

(57) ABSTRACT

A monobloc aerosol tube or can being coated on at least a portion of an internal surface thereof with a coating composition, the coating composition comprising a thermoset powder composition, wherein the coating composition is substantially free of bisphenol A (BPA), bisphenol F (BPF), bisphenol A diglycidyl ether (BADGE) and bisphenol F diglycidyl ether (BFDGE); wherein the thermoset powder composition comprises an acid functional polyester material and a crosslinker material operable to crosslink the acid functionality on the acid functional polyester material.

19 Claims, No Drawings

Related U.S. Application Data application No. 14/996,838, filed on Jan. 15, 2016, now abandoned.

(51) Int. Cl.
*C08G 18/73* (2006.01)
*B27N 3/00* (2006.01)

(56) References Cited

U.S. PATENT DOCUMENTS

| | | | |
|---|---|---|---|
| 3,663,516 | A | 5/1972 | Vogt |
| 4,211,683 | A | 7/1980 | Wenzel |
| 4,284,572 | A | 8/1981 | Stanley et al. |
| 4,990,579 | A | 5/1991 | Paar |
| 5,030,754 | A | 7/1991 | Speranza et al. |
| 5,047,294 | A | 9/1991 | Schwab et al. |
| 5,574,083 | A | 11/1996 | Brown et al. |
| 5,714,539 | A | 2/1998 | Perez et al. |
| 5,858,549 | A | 1/1999 | Kielbania, Jr. et al. |
| 5,965,466 | A | 10/1999 | Rodrigues |
| 6,051,646 | A | 4/2000 | Nass et al. |
| 6,140,388 | A | 10/2000 | Nass et al. |
| 6,181,311 | B1 | 1/2001 | Hashimoto |
| 6,248,819 | B1 | 6/2001 | Masuda et al. |
| 6,290,867 | B1 | 9/2001 | Kielbania, Jr. et al. |
| 6,875,800 | B2 | 4/2005 | Vanier et al. |
| 6,894,086 | B2 | 5/2005 | Munro et al. |
| 7,033,526 | B2 | 4/2006 | Figiel et al. |
| 7,605,194 | B2 | 10/2009 | Ferencz et al. |
| 8,153,344 | B2 | 4/2012 | Faler et al. |
| 8,846,156 | B2 | 9/2014 | Swarup et al. |
| 2004/0266921 | A1 | 12/2004 | Rodrigues et al. |
| 2005/0113269 | A1 | 5/2005 | Landa et al. |
| 2005/0171300 | A1 | 8/2005 | Moens et al. |
| 2008/0004361 | A1 | 1/2008 | Palermo |
| 2009/0197202 | A1 | 8/2009 | Matsumura |
| 2009/0246343 | A1 | 10/2009 | Wu et al. |
| 2011/0070372 | A1 | 3/2011 | Faucher et al. |
| 2011/0070374 | A1 | 3/2011 | Ambrose et al. |
| 2011/0151128 | A1 | 6/2011 | Boggs et al. |
| 2011/0244157 | A1 | 10/2011 | Singer et al. |
| 2014/0011018 | A1 | 1/2014 | Diehl et al. |
| 2014/0023782 | A1 | 1/2014 | Kunz et al. |
| 2014/0030535 | A1 | 1/2014 | Makotky et al. |
| 2014/0319133 | A1 | 10/2014 | Castelberg et al. |
| 2015/0225339 | A1 | 8/2015 | Niedermair et al. |
| 2015/0344732 | A1 | 12/2015 | Witt-Sanson et al. |
| 2016/0280951 | A1 | 9/2016 | Drumright et al. |

FOREIGN PATENT DOCUMENTS

| | | |
|---|---|---|
| CN | 102296290 A | 12/2011 |
| CN | 103145588 A | 6/2013 |
| CN | 103502354 A | 1/2014 |
| CN | 104955911 A | 9/2015 |
| EP | 0519186 A1 | 12/1992 |
| EP | 0866082 A1 | 9/1998 |
| EP | 1525274 B1 | 4/2005 |
| EP | 1541640 A1 | 6/2005 |
| EP | 1935878 A1 | 6/2008 |
| EP | 2316868 A1 | 5/2011 |
| EP | 2447059 A2 | 5/2012 |
| EP | 2746353 A1 | 6/2014 |
| EP | 2773710 A1 | 9/2014 |
| JP | H11335594 A | 12/1999 |
| JP | 2001192609 A | 7/2001 |
| JP | 5146327 B2 | 2/2013 |
| JP | 2014148618 A | 8/2014 |
| RU | 2376284 C1 | 10/2009 |
| RU | 2009103017 A | 8/2010 |
| WO | 2004000958 A1 | 12/2003 |
| WO | 2006132910 A1 | 12/2006 |
| WO | 2008076669 A1 | 6/2008 |
| WO | 2009095471 A1 | 8/2009 |
| WO | 2011019840 A1 | 2/2011 |
| WO | 2012118500 A1 | 9/2012 |
| WO | 2012118501 A1 | 9/2012 |
| WO | 2012162301 A1 | 11/2012 |
| WO | 2013191825 A1 | 12/2013 |
| WO | 2014025411 A1 | 2/2014 |
| WO | 2015077687 A1 | 5/2015 |

OTHER PUBLICATIONS

Machine English translation of CN103145588.
Machine English translation of EP0519186.
Machine English translation of the Abstract only of JP2001192609.
Machine English translation of JPH11335594.
Machine English translation of RU2376284.
Machine English translation of RU2009103017.

MONOBLOC AEROSOL TUBE OR CAN HAVING A COATING COMPOSITION

The present invention relates to monobloc aerosol tubes or cans having a coating composition thereon, in particular on at least a portion of an internal surface thereof.

Cans used for the storage of aerosols, such as personal healthcare aerosols, are typically formed from a tube, for example, an aluminium tube. One such tube type is a monobloc aerosol, which is so called because it is formed from a single piece (a small disc known as a "slug") of aluminium.

The surfaces of such cans are coated for various reasons. The external surfaces of such cans are often coated in a decorative manner and may allow printing thereon to inform a user as to the contents of the can. The internal surfaces of such cans are typically coated to protect the can from the contents therein (the contents to be delivered from the can and the propellant), which in some instances may be chemically aggressive. The coating on the can should also protect the contents from the can. There should be a minimal amount of alteration to the contents from materials that are products of erosion of the can, or from the coating itself. Accordingly, the coating composition used to coat the internal surfaces of the can should be designed such that it is able to withstand contact with these aggressive chemicals and to minimise the release of material from the metal of the can or the coating layer into the contents of the can.

Furthermore, many of the coating compositions currently used for monobloc aerosol tubes or can contain epoxy resins. Such epoxy resins are typically formed from polyglycidyl ethers of bisphenol A (BPA). BPA is perceived as being harmful to human health and it is therefore desirable to eliminate it from coatings. Derivatives of BPA such as diglycidyl ethers of bisphenol A (BADGE), epoxy novolak resins and polyols prepared from BPA and bisphenol F (BPF) are also viewed as problematic.

Therefore, there is a desire to provide coating compositions for use in monobloc aerosol tube or can internals that are able to withstand aggressive chemicals that are stored in such cans, while avoiding certain components, such as BPA and its derivatives, and/or solvents.

According to a first aspect of the present invention there is provided a monobloc aerosol tube or can being coated on at least a portion of an internal surface thereof with a coating composition, the coating composition comprising a thermoset powder composition, wherein the coating composition is substantially free of bisphenol A (BPA), bisphenol F (BPF), bisphenol A diglycidyl ether (BADGE) and bisphenol F diglycidyl ether (BFDGE); wherein the thermoset powder composition comprises an acid functional polyester material and a crosslinker material operable to crosslink the acid functionality on the acid functional polyester material.

Suitably, the thermoset powder composition comprises:
a) an acid functional polyester material, suitably having an acid number of at least 25 mg KOH/g, and
b) a crosslinker material operable to crosslink the acid functionality on the acid functional polyester material.

"Powder" and like terms, as used herein, refers to materials that are in the form of solid particulates, as opposed to materials which are in the liquid form.

The thermoset powder of the present invention comprises an acid-functional polyester material (a). The acid functional polyester material suitably comprises the reaction product of a polyacid and a polyol.

Polyacid and like terms, as used herein, refers to a compound having two or more carboxylic acid groups, such as two, three or four acid groups, and includes an ester of the polyacid (wherein one or more of the acid groups is esterified) or an anhydride. The polyacid is suitably an organic polyacid.

Suitably, the carboxylic acid groups of the polyacid may be connected by a bridging group selected from: an alkylene group; an alkenylene group; an alkynylene group; or an arylene group.

The acid functional polyester material may be formed from any suitable polyacid. Suitable examples include, but are not limited to one or more of the following: diacids such as, for example, maleic acid, fumaric acid, itaconic acid, adipic acid, azelaic acid, succinic acid, sebacic acid, glutaric acid, decanoic diacid, dodecanoic diacid, phthalic acid, isophthalic acid, 5-tert-butylisophthalic acid, tetrachlorophthalic acid, tetrahydrophthalic acid, naphthalene dicarboxylic acid, terephthalic acid, hexahydrophthalic acid, methylhexahydrophthalic acid, dimethyl terephthalate, cyclohexane dicarboxylic acid, chlorendic anhydride, 1,3-cyclohexane dicarboxylic acid, 1,4-cyclohexane dicarboxylic acid, endomethylene tetrahydrophthalic acid and endoethylene hexahydrophthalic acid; triacids such as, for example, trimellitic acid; polyacids such as, for example, naphthalene tetracarboxylic acid, cyclohexanetetra carboxylic acid, cyclobutane tetracarboxylic and tricyclodecane polycarboxylic acid; esters and anhydrides of all the aforementioned acids and combinations thereof.

The polyacid may be selected from terephthalic acid; isophthalic acid; adipic acid; trimellitic anhydride; or combinations thereof.

The polyacid may comprise terephthalic acid and/or isophthalic acid. The polyacid may comprise at least 50 mol %, suitably at least 60 mol %, such as at least 70 mol %, or even at least 75 mol % of terephthalic acid and/or isophthalic acid based on the total number of moles of polyacid. The polyacid may comprise up to 100 mol %, suitably up to 95 mol %, such as up to 90 mol % of terephthalic acid and/or isophthalic acid based on the total number of moles of polyacid. The polyacid may comprise from 50 to 100 mol %, suitably from 60 to 100 mol %, such as from 70 to 100 mol %, or even from 75 to 100 mol % of terephthalic acid and/or isophthalic acid based on the total number of moles of polyacid. The polyacid may comprise from 50 to 95 mol %, suitably from 60 to 95 mol %, such as from 70 to 95 mol %, or even from 75 to 95 mol % of terephthalic acid and/or isophthalic acid based on the total number of moles of polyacid. The polyacid may comprise from 50 to 90 mol %, suitably from 60 to 90 mol %, such as from 70 to 90 mol %, or even from 75 to 90 mol % of terephthalic acid and/or isophthalic acid based on the total number of moles of polyacid. Suitably, the polyacid may comprise from 75 to 90 mol % of terephthalic acid and/or isophthalic acid based on the total number of moles of polyacid.

The polyacid may comprise a diacid. The diacid may comprise at least 60 mol %, suitably at least 70 mol %, such as at least 80 mol %, or even 85 mol % of terephthalic acid and/or isophthalic acid based on the total number of moles of diacid. The diacid may comprise up to 100 mol %, suitably up to 99.9 mol %, such as at least 99 mol %, or even up to 95 mol % of terephthalic acid and/or isophthalic acid based on the total number of moles of diacid. The polyacid may comprise from 60 to 100 mol %, suitably from 70 to 100 mol %, such as from 80 to 100 mol %, or even from 80 to 100 mol % of terephthalic acid and/or isophthalic acid based on the total number of moles of diacid. That polyacid may comprise from 60 to 99.9 mol %, suitably from 70 to 99.9 mol %, such as from 80 to 99.9 mol %, or even from 80 to 99.9 mol % of terephthalic acid and/or isophthalic acid based on the total number of moles of diacid. The polyacid may comprise from 60 to 99 mol %, suitably from 70 to 99 mol %, such as from 80 to 99 mol %, or even from 80 to 99 mol % of terephthalic acid and/or isophthalic acid based on the total number of moles of diacid. The polyacid may comprise from 60 to 95 mol %, suitably from 70 to 95 mol %, such as from 80 to 95 mol %, or even from 80 to 95 mol % of terephthalic acid and/or isophthalic acid based on the total number of moles of diacid. Suitably, the diacid may comprise from 75 to 100 mol % of terephthalic acid and/or isophthalic acid based on the total number of moles of diacid.

"Polyol" and like terms, as used herein, refers to a compound having two or more hydroxyl groups, such as two, three or four hydroxyl groups. The hydroxyl groups of the polyol may be connected by a bridging group selected from: an alkylene group; an alkenylene group; an alkynylene group; or an arylene group. Suitably the polyol is an organic polyol.

The acid functional polyester material may be formed from any suitable polyol. Suitable examples include, but are not limited to one or more of the following: diols such as, for example, alkylene glycols, such as ethylene glycol, diethylene glycol, dipropylene glycol, triethylene glycol, tripropylene glycol, hexylene glycol, polyethylene glycol, polypropylene glycol and neopentyl glycol; hydrogenated bisphenol A; cyclohexanediol; propanediols including 1,2-propanediol, 1,3-propanediol, butyl ethyl propanediol and 2-ethyl-2-butyl-1,3-propanediol; butanediols including 1,4-butanediol, 1,3-butanediol, butane-2,3-diol, 2-methyl-1,3-propanediol, tricyclodecane dimethanol-2,2,4,4-tetramethyl cyclobutane-1,3-diol and 2-ethyl-1,4-butanediol; pentanediols including trimethyl pentanediol and 2-methylpentanediol; cyclohexanedimethanol; hexanediols including 1,6-hexanediol, caprolactonediol (for example, the reaction product of epsilon-caprolactone and ethylene glycol); hydroxyalkylated bisphenols; polyether glycols, for example, poly(oxytetramethylene) glycol; dimethylol cyclohexane; triols such as, for example, trimethylol propane, trimethylol ethane, trimethylol butane and glycerol; polyols such as, for example, pentaerythritol and di-pentaerythritol; and the like or combinations thereof.

The polyester material may be formed from an unsaturated polyol. Suitable examples of unsaturated polyols include, but are not limited to one or more of the following: trimethylol propane monoallyl ether; trimethylol ethane monoallyl ether; prop-1-ene-1,3-diol or combinations thereof.

The polyol may be selected from neopentyl glycol; ethylene glycol; diethylene glycol; or combinations thereof.

The polyol may comprise neopentyl glycol. The polyol may comprise at least 10 mol %, suitably at least 20 mol %, such as at least 30 mol %, such as 40 mol %, or even at least 50 mol % of neopentyl glycol based on the total number of moles of polyol. The polyol may comprise up to 100 mol %, suitably up to 90 mol %, such as up to 80 mol %, or even up to 70 mol % of neopentyl glycol based on the total number of moles of polyol present. The polyol may comprise from 10 to 100 mol %, suitably from 10 to 90 mol %, such as from 10 to 80 mol %, or even from 10 to 70 mol % of neopentyl glycol based on the total number of moles of polyol present. The polyol may comprise from 20 to 100 mol %, suitably from 20 to 90 mol %, such as from 20 to 80 mol %, or even from 20 to 70 mol % of neopentyl glycol based on the total number of moles of polyol present. The polyol may comprise from 30 to 100 mol %, suitably from 30 to 90 mol %, such as from 30 to 80 mol %, or even from 30 to 70 mol % of neopentyl glycol based on the total number of moles of polyol present. The polyol may comprise from 40 to 100 mol %, suitably from 40 to 90 mol %, such as from 40 to 80 mol %, or even from 40 to 70 mol % of neopentyl glycol based on the total number of moles of polyol present. The polyol may comprise from 50 to 100 mol %, suitably from 50 to 90 mol %, such as from 50 to 80 mol %, or even from 50 to 70 mol % of neopentyl glycol based on the total number of moles of polyol present. Suitably, the polyol may comprise from 50 to 70 mol % of neopentyl glycol based on the total number of moles of polyol present.

The polyol may comprise a diol. The diol may comprise at least 10 mol %, suitably at least 20 mol %, such as at least 30 mol %, such as 40 mol %, or even at least 50 mol % of neopentyl glycol based on the total number of moles of diol. The diol may comprise up to 100 mol %, suitably up to 90 mol %, such as up to 80 mol %, or even up to 70 mol % of neopentyl glycol based on the total number of moles of diol present. The diol may comprise from 10 to 100 mol %, suitably from 10 to 90 mol %, such as from 10 to 80 mol %, or even from 10 to 70 mol % of neopentyl glycol based on the total number of moles of diol present. The diol may comprise from 20 to 100 mol %, suitably from 20 to 90 mol %, such as from 20 to 80 mol %, or even from 20 to 70 mol % of neopentyl glycol based on the total number of moles of diol present. The diol may comprise from 30 to 100 mol %, suitably from 30 to 90 mol %, such as from 30 to 80 mol %, or even from 30 to 70 mol % of neopentyl glycol based on the total number of moles of diol present. The diol may comprise from 40 to 100 mol %, suitably from 40 to 90 mol %, such as from 40 to 80 mol %, or even from 40 to 70 mol % of neopentyl glycol based on the total number of moles of diol present. The diol may comprise from 50 to 100 mol %, suitably from 50 to 90 mol %, such as from 50 to 80 mol %, or even from 50 to 70 mol % of neopentyl glycol based on the total number of moles of diol present. Suitably, the diol may comprise from 50 to 70 mol % of neopentyl glycol based on the total number of moles of diol present.

The term "alk" or "alkyl", as used herein unless otherwise defined, relates to saturated hydrocarbon radicals being straight, branched, cyclic or polycyclic moieties or combinations thereof and contain 1 to 20 carbon atoms, suitably 1 to 10 carbon atoms, more suitably 1 to 8 carbon atoms, still more suitably 1 to 6 carbon atoms, yet more suitably 1 to 4 carbon atoms. These radicals may be optionally substituted with a chloro, bromo, iodo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$, $C(S)NR^{25}R^{26}$, aryl or Het, wherein $R^{19}$ to $R^{27}$ each independently represent hydrogen, aryl or alkyl, and/or be interrupted by one or more oxygen or sulphur atoms, or by silano or dialkylsiloxane groups. Examples of such radicals may be independently selected from methyl, ethyl, n-propyl, isopropyl, n-butyl, isobutyl, sec-butyl, tert-butyl, 2-methylbutyl, pentyl, iso-amyl, hexyl, cyclohexyl, 3-methylpentyl, octyl and the like. The term "alkylene", as used herein, relates to a bivalent radical alkyl group as defined above. For example, an alkyl group such as methyl which would be represented as —$CH_3$, becomes methylene, —$CH_2$—, when represented as an alkylene. Other alkylene groups should be understood accordingly.

The term "alkenyl", as used herein, relates to hydrocarbon radicals having one or several, suitably up to 4, double bonds, being straight, branched, cyclic or polycyclic moieties or combinations thereof and containing from 2 to 18 carbon atoms, suitably 2 to 10 carbon atoms, more suitably from 2 to 8 carbon atoms, still more suitably 2 to 6 carbon atoms, yet more suitably 2 to 4 carbon atoms. These radicals may be optionally substituted with a hydroxyl, chloro, bromo, iodo, cyano, nitro, $OR^{19}$, $OC(O)R^{20}$, $C(O)R^{21}$, $C(O)OR^{22}$, $NR^{23}R^{24}$, $C(O)NR^{26}R^{26}$, $SR^{27}$, $C(O)SR^{27}$, $C(S)NR^{25}R^{26}$, or aryl, wherein $R^{19}$ to $R^{27}$ each independently represent hydrogen, aryl or alkyl, and/or be interrupted by one or more oxygen or sulphur atoms, or by silano or dialkylsiloxane groups. Examples of such radicals may be independently selected from alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like. The term "alkenylene", as used herein, relates to a bivalent radical alkenyl group as defined above. For example, an alkenyl group such as ethenyl which would be represented as —CH═CH2, becomes ethenylene, —CH═CH—, when represented as an alkenylene. Other alkenylene groups should be understood accordingly.

The term "alkynyl", as used herein, relates to hydrocarbon radicals having one or several, suitably up to 4, triple bonds, being straight, branched, cyclic or polycyclic moieties or combinations thereof and having from 2 to 18 carbon atoms, suitably 2 to 10 carbon atoms, more suitably from 2 to 8 carbon atoms, still more suitably from 2 to 6 carbon atoms, yet more suitably 2 to 4 carbon atoms. These radicals may be optionally substituted with a hydroxy, chloro, bromo, iodo, cyano, nitro, $OR^{19}$, $OC(O)R^{20}$, $C(O)R^{21}$, $C(O)OR^{22}$, $NR^{23}R^{24}$, $C(O)NR^{26}R^{26}$, $SR^{27}$, $C(O)SR^{27}$, $C(S)NR^{25}R^{26}$, or aryl, wherein $R^{19}$ to $R^{27}$ each independently represent hydrogen, aryl or lower alkyl, and/or be interrupted by one or more oxygen or sulphur atoms, or by silano or dialkylsiloxane groups. Examples of such radicals may be independently selected from alkynyl radicals include ethynyl, propynyl, propargyl, butynyl, pentynyl, hexynyl and the like. The term "alkynylene", as used herein, relates to a bivalent radical alkynyl group as defined above. For example, an alkynyl group such as ethynyl which would be represented as —C≡CH, becomes ethynylene, —C≡C—, when represented as an alkynylene. Other alkynylene groups should be understood accordingly.

The term "aryl", as used herein, relates to an organic radical derived from an aromatic hydrocarbon by removal of one hydrogen, and includes any monocyclic, bicyclic or polycyclic carbon ring of up to 7 members in each ring, wherein at least one ring is aromatic. These radicals may be optionally substituted with a hydroxy, chloro, bromo, iodo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{27}$, $C(O)SR^{27}$, $C(S)NR^{25}R^{26}$, or aryl, wherein $R^{19}$ to $R^{27}$ each independently represent hydrogen, aryl or lower alkyl, and/or be interrupted by one or more oxygen or sulphur atoms, or by silano or dialkylsilcon groups. Examples of such radicals may be independently selected from phenyl, p-tolyl, 4-methoxyphenyl, 4-(tert-butoxy)phenyl, 3-methyl-4-methoxyphenyl, 4-fluorophenyl, 4-chlorophenyl, 3-nitrophenyl, 3-aminophenyl, 3-acetamidophenyl, 4-acetamidophenyl, 2-methyl-3-acetamidophenyl, 2-methyl-3-aminophenyl, 3-methyl-4-aminophenyl, 2-amino-3-methylphenyl, 2,4-dimethyl-3-aminophenyl, 4-hydroxyphenyl, 3-methyl-4-hydroxyphenyl, 1-naphthyl, 2-naphthyl, 3-amino-1-naphthyl, 2-methyl-3-amino-1-naphthyl, 6-amino-2-naphthyl, 4,6-dimethoxy-2-naphthyl, tetrahydronaphthyl, indanyl, biphenyl, phenanthryl, anthryl or acenaphthyl and the like. The term "arylene", as used herein, relates to a bivalent radical aryl group as defined above. For example, an aryl group such as phenyl which would be represented as -Ph, becomes phenylene, -Ph-, when represented as an arylene. Other arylene groups should be understood accordingly.

For the avoidance of doubt, the reference to alkyl, alkenyl, alkynyl, aryl or aralkyl in composite groups herein should be interpreted accordingly, for example the reference to alkyl in aminoalkyl or alk in alkoxyl should be interpreted as alk or alkyl above etc.

The acid functional polyester material may be formed from any suitable molar ratio of polyacid to polyol. The molar ratio of polyacid to polyol in the polyester material may be from 20:1 to 1:20, suitably from 10:1 to 1:10, such as from 5:1 to 1:5, or even from 2:1 to 1:2. Suitably, the molar ratio of polyacid to polyol in the polyester material may be 1:1.

The acid functional polyester material may comprise a polyol comprising a diacid and a triacid and a diol. It will be appreciated by a person skilled in the art that the amount of triacid present will influence the acid number of the acid functional polyester material.

The acid functional polyester material may optionally be formed from one or more additional monomers. Suitably, the acid functional polyester material may optionally include one or more additional monomers selected from monoacids or monohydric alcohols or combinations thereof. Suitably, the optional additional monomers may be organic.

The acid functional polyester material may optionally be formed from an additional monoacid. "Monoacid", and like terms as used herein, refers to compounds having one carboxylic acid group and includes an ester of the monoacid (where the acid group is esterified) or an anhydride. The monoacid is suitably an organic monoacid.

The acid functional polyester material may optionally be formed from any suitable additional monoacid. Suitable examples include, but are not limited to one or more of the following: benzoic acid; cyclohexane carboxylic acid; tricyclodecane carboxylic acid; camporic acid; benzoic acid; t-butyl benzoic acid; $C_1$-$C_{18}$ aliphatic carboxylic acids such as acetic acid; propanoic acid; butanoic acid; hexanoic acid; oleic acid; linoleic acid; undecanoic acid; lauric acid; isononanoic acid; fatty acids; hydrogenated fatty acids of naturally occurring oils; esters and/or anhydrides of any of the aforementioned acids and combinations thereof.

The acid functional polyester material may optionally be formed from an additional monohydric alcohol. "Monohydric alcohol" and like terms as used herein, refers to compounds having one hydroxyl group. Suitably, the monohydric alcohol is an organic monohydric alcohol.

The acid functional polyester material may optionally be formed from any suitable additional monohydric alcohol. Suitable examples include but are not limited to one or more of the following: benzyl alcohol; hydroxyethoxybenzene; methanol; ethanol; propanol; butanol; pentanol; hexanol; heptanol; dodecyl alcohol; stearyl alcohol; oleyl alcohol; undecanol; cyclohexanol; phenol; phenyl carbinol; methylphenyl carbinol; cresol; monoethers of glycols; halogen-substituted or other substituted alcohols and combinations thereof.

The acid functional polyester material may have an acid number (AN) of at least 25 mg KOH/g. Suitably, the polyester material may have an acid number from 25 to 100 mg KOH/g, such as from 30 to 100 mg KOH/g or even from 50 to 90 mg KOH/g. The acid functional polyester material may have an acid number from 50 to 80 mg KOH/g.

The acid functional polyester material may have an acid number from 65 to 75 mg KOH/g.

The acid functional polyester material may have an acid number from 30 to 40 mg KOH/g.

Suitably, the acid number is expressed on solids.

The acid number (AN) of the acid functional polyester material may be measured by any suitable method. Methods to measure AN will be well known to a person skilled in the art. Suitably, the AN is determined by titration with 0.1M methanolic potassium hydroxide (KOH) solution. In such a method, a sample of solid polyester (typically, 0.1 to 3 g) is weighed accurately into a conical flask and is dissolved, using light heating and stirring as appropriate, in 25 ml of dimethyl formamide containing phenolphthalein indicator. The solution is then cooled to room temperature and titrated with the 0.1M methanolic potassium hydroxide solution. The resulting acid number is expressed in units of mg KOH/g and is calculated using the following equation:

$$\text{Acid number} = \frac{\text{titre of KOH solution(ml)} \times \text{molarity KOH solution(M)} \times 56.1}{\text{weight of solid sample(g)}}$$

All values for acid number reported herein were measured in this way.

The acid functional polyester material may have any suitable gross hydroxyl value (OHV). The acid functional polyester material may have a gross OHV up to 5.0 mg KOH/g. Suitably, the acid functional polyester material may have a gross OHV from 0 to 5.0 mg KOH/g, such as from 0 to 0.4 KOH/g or even from 0 to 3.0 KOH/g.

Suitably, the gross hydroxyl value (OHV) is expressed on solids.

The gross hydroxyl value (OHV) of the acid functional polyester material may be measured by any suitable method. Methods to measure OHV will be well known to a person skilled in the art. Suitably, the hydroxyl value is the number of mg of KOH equivalent to the hydroxyl groups in 1 g of material. In such a method, suitably, a sample of solid polyester (typically, 0.1 to 3 g) is weighed accurately into a conical flask and is dissolved, using light heating and stirring as appropriate, in 20 ml of tetrahydrofuran. 10 ml of 0.1M 4-(dimethylamino)pyridine in tetrahydrofuran (catalyst solution) and 5 ml of a 9 vol % solution of acetic anhydride in tetrahydrofuran (i.e. 90 ml acetic anhydride in 910 ml tetrahydrofuran; acetylating solution) are then added to the mixture. After 5 minutes, 10 ml of an 80 vol % solution of tetrahydrofuran (i.e. 4 volume parts tetrahydrofuran to 1 part distilled water; hydrolysis solution) us added. After 15 minutes, 10 ml tetrahydrofuran is added and the solution is titrated with 0.5M ethanolic potassium hydroxide (KOH). A blank sample is also run where the sample of solid polyester is omitted. The resulting hydroxyl number is expressed in units of mg KOH/g and is calculated using the following equation:

$$\text{Hydroxyl value} = \frac{(V_2 - V_1) \times \text{molarity of KOH solution(M)} \times 56.1}{\text{weight of solid sample(g)}}$$

wherein $V_1$ is the titre of KOH solution (ml) of the polyester sample and $V_2$ is the titre of KOH solution (ml) of the blank sample. All values for gross hydroxyl value reported herein were measured in this way.

The acid functional polyester material may have any suitable glass transition temperature (Tg). The acid functional polyester material may have a Tg of at least 20° C., suitably at least 30° C., such as at least 40° C., or even at least 50° C. The acid functional polyester material may have a Tg of up to 150° C., suitably up to 120° C., such as up to 100° C., or even up to 80° C. The acid functional polyester material may have a Tg from 20° C. to 150° C., suitably from 20° C. to 120° C., such as from 20° C. to 100° C., or even from 20° C. to 80° C. The acid functional polyester material may have a Tg from 30° C. to 150° C., suitably from 30° C. to 120° C., such as from 30° C. to 100° C., or even from 30° C. to 80° C. The acid functional polyester material may have a Tg from 40° C. to 150° C., suitably from 40° C. to 120° C., such as from 40° C. to 100° C., or even from 40° C. to 80° C. The acid functional polyester material may have a Tg from 50° C. to 150° C., suitably from 50° C. to 120° C., such as from 50° C. to 100° C., or even from 50° C. to 80° C.

Suitably, the acid functional polyester material may have a Tg from 60° C. to 70° C.

The Tg of the acid functional polyester material may be measured by any suitable method. Methods to measure Tg will be well known to a person skilled in the art. Suitably, the Tg is measured according to ASTM D6604-00 (2013) ("Standard Practice for Glass Transition Temperatures of Hydrocarbon Resins by Differential Scanning Calorimetry". Heat-flux differential scanning calorimetry (DSC), sample pans: aluminium, reference: blank, calibration: indium and mercury, sample weight: 10 mg, heating rate: 20° C./min). All values for Tg reported herein were measured in this way unless specified otherwise.

The acid functional polyester material according to the present invention may have any suitable viscosity at 200° C. The acid functional polyester material may have a viscosity at 200° C. from 2 to 100 Poise, suitably from 5 to 70 Poise, such as from 10 to 50 Poise, or even from 20 to 40 Poise. The acid functional polyester material may have a viscosity at 200° C. of at least 2 Poise, suitably at least 5 Poise, such as at least 10 Poise, or even at least 20 Poise. The acid functional polyester material may have a viscosity at 200° C. of up to 100 Poise, suitably up to 70 Poise, such as up to 50 Poise, or even up to 40 Poise. The acid functional polyester material may have a viscosity at 200° C. from 2 to 100 Poise, suitably from 2 to 70 Poise, such as from 2 to 50 Poise, or even from 2 to 40 Poise. The acid functional polyester material may have a viscosity at 200° C. from 5 to 100 Poise, suitably from 5 to 70 Poise, such as from 5 to 50 Poise, or even from 5 to 40 Poise. The acid functional polyester material may have a viscosity at 200° C. from 10 to 100 Poise, suitably from 10 to 70 Poise, such as from 10 to 50 Poise, or even from 10 to 40 Poise. The acid functional polyester material may have a viscosity at 200° C. from 20 to 100 Poise, suitably from 20 to 70 Poise, such as from 20 to 50 Poise, or even from 20 to 40 Poise.

The viscosity of the acid functional polyester material may be measured by any suitable method. Methods to measure viscosity, sometimes referred to as melt viscosity, will be well known to a person skilled in the art. In such a method, suitably, viscosity is determined using a cone and plate viscometer with a heated plate with cones which can be selected together with appropriate rotational speeds to measure viscosities within the desired ranges. Suitably, a Brookfield CAP 2000+ machine which is capable of measuring viscosities at temperatures of 100 to 250° C. is used. The temperature selected for the measurement is held constant throughout the measurement time and the detail of the temperature used is suitably recorded for each measurement. Suitably, the cone used is a spindle no. 6 and the speed of rotation is selected so as to ensure that the range of measurements falls well within the total measurement range. All values for viscosity reported herein were measured in this way.

The acid functional polyester material of the present invention may have any suitable number-average molecular weight (Mn). The acid functional polyester material may have an Mn from 500 Daltons (Da=g/mole), suitably from 1,000 Da, such as from 2,000 Da or even from 5,000 Da. The acid functional polyester material may have an Mn up to 200,000 Da, suitably up to 100,000 Da, such as up to 50,000 Da or even up to 20,000 Da.

The acid functional polyester material may have an Mn from 500 to 200,000 Da, suitably from 1,000 to 200,000 Da, such as from 2,000 to 200,000 Da or even from 5,000 to 200,000 Da. The acid functional polyester material may have an Mn from 500 to 100,000 Da, suitably from 1,000 to 100,000 Da, such as from 2,000 to 100,000 Da or even from 5,000 to 100,000 Da. The acid functional polyester material may have an Mn from 500 to 50,000 Da, suitably from 1,000 to 50,000 Da, such as from 2,000 to 50,000 Da or even from 5,000 to 50,000 Da. The acid functional polyester material may have an Mn from 500 to 20,000 Da, suitably from 1,000 to 20,000 Da, such as from 2,000 to 20,000 Da or even from 5,000 to 20,000 Da.

The number-average molecular weight (Mn) may be measured by any suitable method. Techniques to measure the number-average molecular weight will be well known to a person skilled in the art. Suitably, the Mn may be determined by gel permeation chromatography using a polystyrene standard according to ASTM D6579-11 ("Standard Practice for Molecular Weight Averages and Molecular Weight Distribution of Hydrocarbon, Rosin and Terpene Resins by Size Exclusion Chromatography". UV detector; 254 nm, solvent: unstabilised THF, retention time marker: toluene, sample concentration: 2 mg/ml). All values for the number average molecular weight (Mn) and the weight average molecular weight (Mw) reported herein were measured in this way.

The acid functional polyester material of the present invention may have any suitable weight-average molecular weight (Mw). The acid functional polyester material may have an Mw from 500 Daltons (Da=g/mole), suitably from 1,000 Da, such as from 2,000 Da or even from 5,000 Da. The acid functional polyester material may have an Mw up to 200,000 Da, suitably up to 100,000 Da, such as up to 50,000 Da or even up to 20,000 Da.

The acid functional polyester material may have an Mw from 500 to 200,000 Da, suitably from 1,000 to 200,000 Da, such as from 2,000 to 200,000 Da or even from 5,000 to 200,000 Da. The acid functional polyester material may have an Mw from 500 to 100,000 Da, suitably from 1,000 to 100,000 Da, such as from 2,000 to 100,000 Da or even from 5,000 to 100,000 Da. The acid functional polyester material may have an Mw from 500 to 50,000 Da, suitably from 1,000 to 50,000 Da, such as from 2,000 to 50,000 Da or even from 5,000 to 50,000 Da. The acid functional polyester material may have an Mw from 500 to 20,000 Da, suitably from 1,000 to 20,000 Da, such as from 2,000 to 20,000 Da or even from 5,000 to 20,000 Da.

A person skilled in the art will appreciate that techniques to measure the number-average molecular weight may also be applied to measure the weight-average molecular weight.

The acid functional polyester material according to any aspect of the present invention may be in solid form at room temperature and at atmospheric pressure.

The thermoset powder of the present invention comprises a crosslinker material. The crosslinker material is operable to crosslink the acid functionality on the acid functional polyester material.

Suitable crosslinker materials operable to crosslink the acid functionality on the acid functional polyester material will be well known to the person skilled in the art. Suitable crosslinker materials include, but are not limited to, one or more of the following: phenolic resins (or phenol-formaldehyde resins); aminoplast resins (or triazine-formaldehyde resins); amino resins; epoxy resins; epoxy-mimic resins, such as those based on bisphenols and other bisphenol A (BPA) replacements; isocyanate resins, isocyanurate resins, such as triglycidylisocyanurate; hydroxy (alkyl) amide resins, such as β-hydroxy (alkyl) amide resins; hydroxy(alkyl) urea resins; carbodiimide resins; oxazolines; and combinations thereof.

The crosslinker material may be selected from hydroxy (alkyl) amide resins, such as β-hydroxy (alkyl) amide resins; hydroxy(alkyl) urea resins; carbodiimide resins, such as polycarbodiimide resins; oxazolines; isocyanurate resins, such as triglycidylisocyanurate; epoxy-mimic resins, such as those based on bisphenols and other bisphenol A (BPA) replacements; or combinations thereof. Suitably, the crosslinker material may be selected from hydroxy (alkyl) amide resins, such as β-hydroxy (alkyl) amide resins and/or hydroxy(alkyl) urea resins and/or carbodiimide resins. Suitably, the crosslinker material may be selected from hydroxy (alkyl) amide resins, such as β-hydroxy (alkyl) amide resins and/or hydroxy(alkyl) urea resins.

Suitably, the crosslinker material comprises a hydroxyalkylamide material and/or a hydroxyalkylurea material and/or a carbodiimide resin. Suitably, the crosslinker material comprises a hydroxyalkylamide material and/or a hydroxyalkylurea material.

Suitably, the crosslinker material contains nitrogen, which may be in the form of an amine or amide material. The crosslinker may comprise a hydroxyl substituted amine or amide material.

Suitably, the crosslinker material comprises a hydroxyalkylamide material, such as a β-hydroxyalkylamide material.

The crosslinker material may contain a terminal chemical group as shown in Formula I.

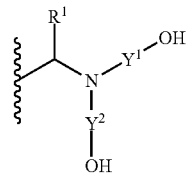

Formula I wherein $R^1$ represents an electron withdrawing group, such as (=O);

and $Y^1$ and $Y^2$ each, independently, represents a $C_1$ to $C_3$ alkylene group.

The terminal chemical group of Formula I may be connected to a further chemical structure, not shown. Additionally or alternatively, the chemical group of formula I may be suspended from a carrier substrate, such as a silica carrier substrate, for example.

The hydroxyalkylamide crosslinker may contain a plurality of terminal chemical groups as shown in Formula I. For example, the hydroxyalkylamide crosslinker may contain 2, 3 or 4 terminal chemical groups as shown in Formula I.

The hydroxyalkylamide crosslinker may comprise a moiety according to Formula II:

Formula II $$\text{HO}\diagdown Y^1 \diagdown N(Y^2\text{OH}) - \overset{R^1}{\underset{}{C}} - X - \overset{R^2}{\underset{}{C}} - N(Y^4\text{OH}) \diagdown Y^3 \diagdown \text{OH}$$

wherein $R^1$ and $R^2$ with reference to Formula II each, independently, represent an electron withdrawing group, such as (=O); $Y^1$, $Y^2$, $Y^3$ and $Y^4$ with reference to Formula II each, independently, represent a $C_1$ to $C_3$ alkylene group; and X is a $C_2$ to $C_6$ alkylene group.

Suitably, each of $R^1$ and $R^2$ with reference to Formula II represents a (=O) group.

Suitably, each of Y1, Y2, Y3 and Y4 with reference to Formula II represent an ethylene group.

Suitably, X represents a butylene group.

Accordingly, the hydroxyalkylamide crosslinker comprises a material of formula III:

Formula III

[Structure of N,N,N',N'-tetrakis(2-hydroxyethyl)adipamide]

The coating composition of the present invention may comprise a commercially available hydroxyalkylamide crosslinker such as, for example, PRIMID XL-552 (available from EMS Chemie); PRIMID QM-1260 (available from EMS Chemie); PRIMID SF-4510 (available from EMS Chemie) and N,N,N',N'-tetrakis(2-hydroxypropyl)adipamide.

The crosslinker may be in the form of a urea material. The crosslinker may comprise a hydroxyl substituted urea material.

Suitably, the crosslinker may comprise a hydroxy functional alkyl polyurea material.

The crosslinker may contain a terminal chemical group as shown in Formula IV.

Formula IV $$\text{\textasciitilde}\!N(H)-\overset{O}{\underset{}{C}}-N(Y^6)-Y^5$$

wherein $Y^5$ and $Y^6$ each, independently, represent hydrogen, an alkyl or a hydroxy functional alkyl having two or more carbon atoms and at least one of $Y^5$ and $Y^6$ is a hydroxyl functional alkyl having two or more carbon atoms.

The $Y^5$ and $Y^6$ groups may exclude ether linkages.

The terminal chemical group of Formula IV may be connected to a further chemical structure, not shown. Additionally or alternatively, the chemical group of Formula IV may be suspended from a carrier substrate, such as a silica carrier substrate, for example.

The crosslinker may contain a plurality of terminal chemical groups as shown in Formula IV. For example, the crosslinker may contain 2 to 6 terminal chemical groups as shown in Formula IV, such as 2, 3 or 4 terminal chemical groups as shown in Formula IV.

The crosslinker material may comprise a moiety according to Formula V:

Formula V $$R{-}\!\left(\!\overset{H}{\underset{}{N}}\!-\!\overset{O}{\underset{}{C}}\!-\!N\!\diagdown\!\overset{R_1}{\underset{R_1}{}}\!\right)_{\!n}$$

wherein R with reference to Formula V comprises the residue of an isocyanurate, biuret, allophonate, glycoluril, benzoguanamine, polyetheramine, and/or polymeric moiety having an Mn of 500 or greater; each $R_1$ with reference to Formula V is independently a hydrogen, an alkyl or a hydroxy functional alkyl having 2 or more carbons and at least one $R_1$ with reference to Formula V is a hydroxy functional alkyl having 2 or more carbons; and n is 2-6.

Suitably, the $R_1$ group with reference to Formula V may exclude ether linkages.

The crosslinker may comprise a moiety according to Formula VI:

Formula VI $$R_2{-}\!\left(\!\overset{H}{\underset{}{N}}\!-\!\overset{O}{\underset{}{C}}\!-\!N\!\diagdown\!\overset{R_1}{\underset{R_1}{}}\!\right)_{\!n}$$

wherein $R_2$ with reference to Formula VI comprises a substituted or unsubstituted $C_1$ to $C_{36}$ alkyl group, an aromatic group, or the residue of an isocyanurate, biuret, allophonate, glycoluril, benzoguanamine, polyetheramine, and/or a polymeric moiety having an Mn of 500 or greater; each $R_1$ with reference to Formula VI is independently a hydrogen, an alkyl group having 1 or more carbons, or a hydroxy functional alkyl having 2 or more carbons and at least one $R_1$ with reference to Formula VI is a hydroxy functional alkyl having 2 or more carbons; and n is 2-6.

Suitably, when $R_2$ with reference to Formula VI is a substituted or unsubstituted $C_1$ to $C_{36}$ alkyl group the acid functional polyester material comprises COOH functionality that reacts with the polyurea to form an ester linkage.

Suitably, the $R_1$ group with reference to Formula VI may exclude ether linkages.

It will be understood that when $R_2$ with reference to Formula VI is a substituted or unsubstituted alkyl group, there may be two $R_2$ groups with reference to Formula VI attached to the N, and the two $R_2$ groups with reference to Formula VI may be the same or different. For example, if the hydroxy functional alkyl polyurea is formed from the reaction of dimethyl carbonate with dibutylamine and diisopropanol amine, there will be two $R_2$ groups with reference to Formula VI that will each be C4.

R and $R_2$ with reference to Formula VI may comprise the residue of an isocyanurate, biuret, allophonate, glycoluril, benzoguanamine, polyetheramine and/or polymeric moiety having an Mn of 500 or greater. An isocyanurate will be understood as referring to a compound having three isocyanate groups, typically in ring form, and is sometimes referred to as a trimer. This can include compounds having one or more isocyanurate moieties. Isocyanurates can be purchased from Covestro and Vencore X Chemical. Suitable commercially available isocyanurates include those sold under the trade name DESMODUR such as, for example, DESMODUR N 3300A, DESMODUR N3800, DESMODUR N3790, DESMODUR N3400, DESMODUR N3600, DESMODUR N3900 and DESMODUR RC (commercially available from Covestro), those sold under the trade name VESTANANT such as, for example, VESTANAT T1890/100 (commercially available from Evonik) and those sold under the trade name EASAQUA such as, for example, EASAQUA WT 2102, EASAQUA X D 401, EASAQUA M 501, EASAQUA X D 803, EASAQUA M 502 and EASAQUA X L 600 (commercially available from Vencore X Chemical). Unsaturated isocyanate monomers include but are not limited to 2-acryloyloxyethylisocyanate (AOI), 2-methacryloyloxyethyl isocyanate (MOI), alpha, alpha-dimethyl meta-isopropenyl benzyl isocyanate (TMI), and the adduct of 2-hydroxyethyl acrylate (HEA) and IPDI in 1:1 ratio. A particularly suitable hydroxy functional alkyl polyurea formed from an isocyanurate is shown in Formula VII:

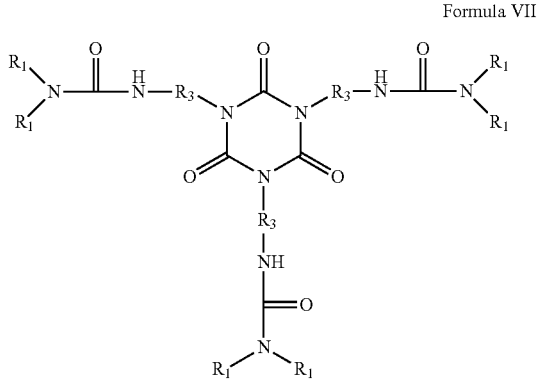

Formula VII wherein $R_1$ with reference to Formula VII is as described above; and each $R_3$ independently comprises an alkyl, aryl, alkylaryl, arylalkyl, alicyclic, and/or polyetheralkyl group.

A particularly suitable hydroxy functional alkyl polyurea formed from a bis-isocyanurate is shown below in Formula VIII:

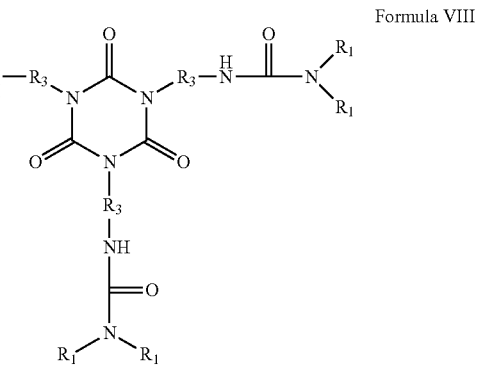

Formula VIII

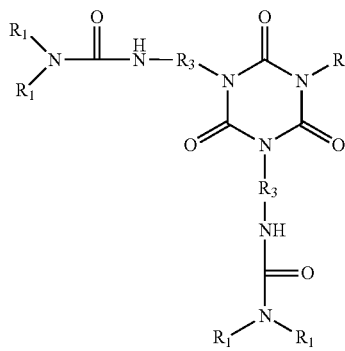

wherein $R_1$ and $R_3$ with reference to Formula VIII are as described above.

A biuret will be understood as referring to a compound that results upon the condensation of two molecules of urea, and is sometimes referred to as a carbamylurea. Biurets are commercial available from Vencore X Chemical and Covestro as, for example, DESMODUR N-75, DESMODUR N-100, and DESMODUR N-3200, HDB 75B, HDB 75M, HDB 75MX, HDB-LV. A particularly suitable hydroxy functional alkyl polyurea formed from a biuret is shown below in Formula IX:

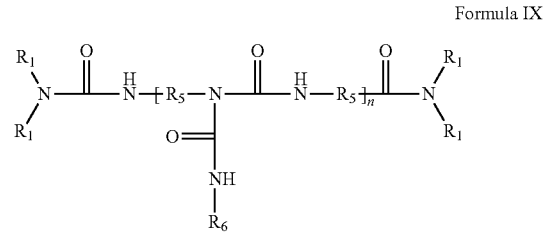

Formula IX wherein $R_1$ with reference to Formula IX is as described above; each $R_5$ independently comprises an alkyl, aryl, alkylaryl, arylalkyl, alicyclic, and/or polyetheralkyl group; and $R_6$ comprises H or an alkyl group.

Uretidione is a dimer of diisocyanate, examples of which include DESMODUR N-3400 polyisocyanate, a blend of the trimer and uretidione of HDI:

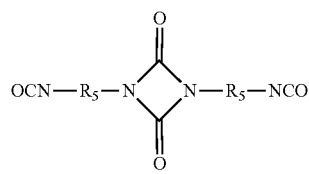

wherein each $R_5$ independently comprises an alkyl, aryl, alkylaryl, arylalkyl, alicyclic, and/or polyetheralkyl group.

An allophonate will be understood as referring to a compound made from urethane and isocyanate. A method for making an allophonate is described at Surface Coating, Vol 1, Raw material and their usage, Landon N.Y., Chapman and Hall, Page 106. The reaction is generally depicted below in scheme I:

Scheme 1

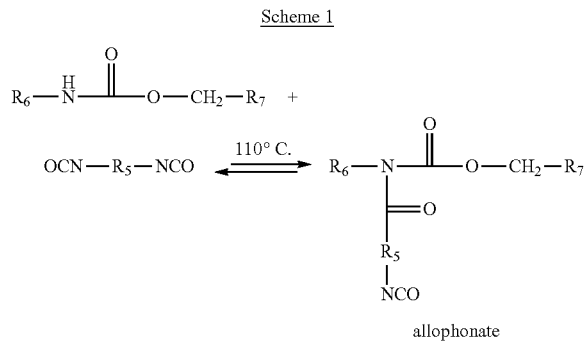

allophonate wherein $R_5$ and $R_6$ with reference to Scheme I are each as described above; and $R_7$ independently comprises the residue of a primary alcohol.

A glycoluril will be understood as referring to a compound composed of two cyclic urea groups joined across the same two-carbon chain, a suitable examples of which includes the below:

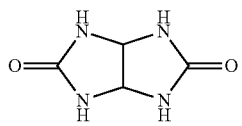

Glycoluril is widely commercially available, such as from Sigma-Aldrich. Benzoguanamine is also known as 6-phenyl-1,3,5-triazine-2,4-diamine and is commercially available from The Chemical Company, Jamestown, R.I.

A polyether amine will be understood as referring to a compound having one or more amine groups attached to a polyether backbone such as one characterized by propylene oxide, ethylene oxide, or mixed propylene oxide and ethylene oxide repeating units in their respective structures, such as, for example, one of the Jeffamine series products. Examples of such polyetheramines include aminated propoxylated pentaerythritols, such as JEFFAMINE XTJ-616, and those represented by Formulas (X) through (VI).

According to Formula (IV) the polyether amine may comprise:

Formula X

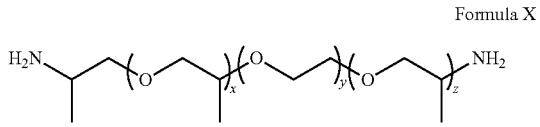

wherein y=0-39, x+z=1-68.

Suitable amine-containing compounds represented by Formula X include, but are not limited to, amine-terminated polyethylene glycol such as those commercially available from Huntsman Corporation in its JEFFAMINE ED series, such as JEFFAMINE HK-511, JEFFAMINE ED-600, JEFFAMINE ED-900 and JEFFAMINE ED-2003, and amine-terminated polypropylene glycol such as in its JEFFAMINE D series, such as JEFFAMINE D-230, JEFFAMINE D-400, JEFFAMINE D-2000 and JEFFAMINE D-4000.

According to Formula XI the polyetheramine may comprise:

Formula XI

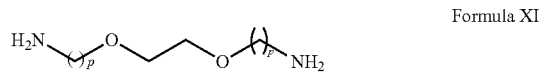

wherein each p independently is 2 or 3.

Suitable amine-containing compounds represented by Formula XI include, but are not limited to, amine-terminated polyethylene glycol based diamines, such as Huntsman Corporation's JEFFAMINE EDR series, such as JEFFAMINE EDR-148 and JEFFAMINE EDR-176.

According to Formula XII the polyetheramine may comprise:

Formula XII

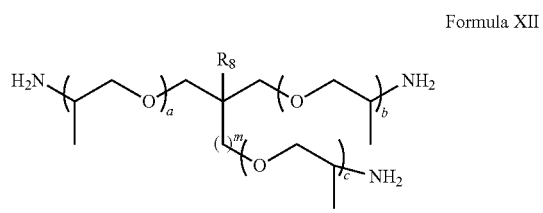

wherein $R_8$ is H or $C_2H_5$, m=0 or 1, a+b+c=5-85.

Suitable amine-containing compounds represented by Formula (VI) include, but are not limited to, amine-terminated propoxylated trimethylolpropane or glycerol, such as Huntsman Corporation's Jeffamine T series, such as JEFFAMINE T-403, JEFFAMINE T-3000 and JEFFAMINE T-5000.

Particularly suitable are di- and tri-amines, such as 4,7,10-trioxa-1,13-tridecanediamine, JEFFAMINE D400, JEFFAMINE D4000, JEFFAMINE D2000, JEFFAMINE T403.

A "polymeric moiety" as used herein in the context of R or $R_2$ with reference to Formulas V to IX refers to any polymer or oligomer to which has been attached two to six hydroxy functional alkyl polyurea groups. The polymer can be, for example, a polyester polyurethane, a polyether polyurethane, or a polyamide polyurethane. The moiety can itself contain functionality, such as acid functionality, hydroxy functionality, and/or amine functionality. The polymeric moiety (which may be oligomeric as noted above) has an Mn of 500 or greater, such as 1000 or greater, 2500 or greater, 4000 or greater, or 5,000 or greater. Mn, as used herein, refers to the number average molecular weight and means the theoretical value as determined by Gel Permeation Chromatography using Waters 2695 separation module with a Waters 410 differential refractometer (RI detector) and polystyrene standards. The Mn values reported according to the invention were determined using this method. Tetrahydrofuran (THF) was used as the eluent at a flow rate of 1 ml min$^{-1}$, and two PL Gel Mixed C columns were used for separation.

In all cases, R and $R_2$ with reference to Formulas V to IX may be substituted or unsubstituted. $R_2$ with reference to Formulas V to IX, as noted above, may also comprise a substituted or unsubstituted $C_1$ to $C_{36}$ alkyl group and/or an aromatic group. For example, the alkyl group may have two to ten carbon atoms, such as six carbon atoms. The alkyl group may derive from an isocyanate, such as a diisocyanate. Suitable examples include isophorone diisocyanate and hexamethylene isocyanate. The aromatic group may derive from an aromatic ring containing isocyanate, suitable examples of which include methylene diphenyl diisocyanate, toluene diisocyanate and tetramethylxylylene diisocyanate.

Certain hydroxy functional alkyl polyureas of, and/or used according to, the invention may be made by reacting an isocyanate-containing compound with amino alcohol. Any isocyanate-containing compound having at least two isocyanate groups can be used, such as any of those described above. It will be appreciated that the "R" or "$R_2$" group with reference to Formulas V to IX will reflect the isocyanate-containing compound selected, if one is used.

Similarly, any amino alcohol having two or more carbon atoms can be used, and the "$R_1$" group with reference to Formulas V to IX will reflect the amino alcohol selected. The amino alcohol can have one, two or more hydroxyl functional groups. One or more amino alcohols can be used, which will result in different $R_1$ groups with reference to Formulas V to IX being present on the polyurea. $R_1$ with reference to Formulas V to IX can also be hydrogen or an alkyl group. Suitable amino alcohols include monoethanol amine, diethanol amine and diisopropanol amine.

The hydroxyl functional alkyl polyureas can be made by reacting amino alcohol with an isocyanate-containing compound in an organic polar solvent, such as alcohol or water. The equivalent ratio of amine to isocyanate may be 2-1:1-2, such as 1:1.

The hydroxy functional alkyl polyureas may be made by alternative methods as well. For example, amino alcohols can react with carbonate to form hydroxylalkyl carbamate, and hydroxylalkyl carbamate can further react with amines to form hydroxy functional alkyl polyureas.

The number-average molecular weight (Mn) of the hydroxy functional alkyl polyurea (even when the polyurea is in the form of a monomer or prepolymer, but not when R or R2 with reference to Formulas V to IX is a polymeric moiety) may be 100 or greater, such as 350 or greater or 1,000 or greater, and/or can be 6,000 or lower, such as 3,000 or lower, or 2,000 or lower. The Mn of the hydroxy functional alkyl polyurea when R or $R_2$ with reference to Formulas V to IX is a polymeric moiety can be 500 or greater, such as 1,000 or greater, 5,000 or greater or 10,000 or greater.

It has surprisingly and advantageously been found by the present inventors that the hydroxyl alkyl urea functional materials typically cure at a lower temperature than, for example, hydroxyalkylamide material, such as a β-hydroxyalkylamide material.

The crosslinker may be in the form of a carbodiimide resin. The crosslinker may comprise a polycarbodiimide. Suitably, the crosslinker may comprise a polycarbodiimide having the following structural units (XIII) or (XIV) including mixtures thereof:

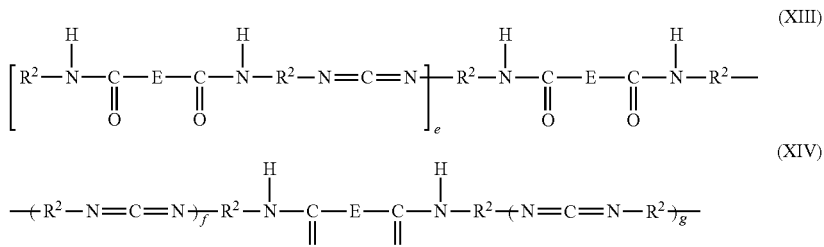

where e is an integer of from 2 to 20; f and g are each at least 1, and f+g is an integer up to 20; E is a radical selected from

where $R^2$ with reference to structural units (XIII) or (XIV) comprises a cyclic radical and $R^3$ with reference to (XV) and (XVI) is a linear hydrocarbon radical containing at least 4 carbon atoms and $R^4$ with reference to (XVI) is hydrogen or an alkyl radical.

The polycarbodiimides may be prepared by reacting an organic group containing a polyisocyanate in the presence of a suitable catalyst to form a polycarbodiimide having terminal NCO-functionality, wherein an active hydrogen-containing compound is added before, during or after polycarbodiimide formation.

The polyisocyanate can be an aliphatic, including cycloaliphatic, or an aromatic polyisocyanate or mixture of the two. Aliphatic including cycloaliphatic polyisocyanates and alkaryl polyisocyanates are particularly suitable. The polyisocyanates can contain from 2 to 4, such as 2 isocyanate groups per molecule. Examples of suitable higher polyisocyanates are 1,2,4-benzene triisocyanate and polymethylene polyphenyl isocyanate. Examples of suitable aromatic diisocyanates are 4,4'-diphenylmethane diisocyanate, 1,3-phenylene diisocyanate, 1,4-phenylene diisocyanate and tolylene diisocyanate. Examples of suitable aliphatic diisocyanates are straight chain aliphatic diisocyanates such as 1,4-tetramethylene diisocyanate and 1,6-hexamethylene diisocyanate and alkaryl polyisocyanates such as m-tetramethylxylene diisocyanate. Also, cycloaliphatic diisocyanates can be employed. Examples include 1,4-cyclohexyl diisocyanate, isophorone diisocyanate, alpha, alpha-xylylene diisocyanate and 4,4-methylene-bis(cyclohexyl isocyanate). Substituted organic group-containing polyisocyanates can also be used in which the substituents are nitro, chloro, alkoxy and other groups that are not reactive with hydroxyl groups or active hydrogens and provided the substituents are not positioned to render the isocyanate group unreactive.

The active hydrogen-containing compound used in the preparation of the polycarbodiimide is suitably a chain extender or spacer linking polyisocyanates together to form NCO-adducts or to link NCO-functional polycarbodiimides together. Any suitable organic compound containing active hydrogens may be used. The term "active hydrogen atoms" refers to hydrogens which, because of their position in the molecule, display activity according to the Zerewitinoff test. Accordingly, active hydrogens include hydrogen atoms attached to oxygen or nitrogen, and thus useful compounds will include those having at least two of these groups (in any combination):

—OH, and —NH$_2$

The moieties attached to each group can be aliphatic, including cycloaliphatic, aromatic, or of a mixed type with aliphatic being particularly suitable.

The active hydrogen-containing material can contain from 2 to 4, particularly suitable 2 active hydrogens per molecule.

Examples of such compounds include amines, which includes polyamines, aminoalcohols, mercapto-terminated derivatives, and alcohols that includes polyhydroxy materials (polyols) that are particularly suitable because of the ease of reaction with polyisocyanates. Also polyols generally give no side reactions, giving higher yields of urethane product with no by-product and the products are hydrolytically stable. Also, with regard to polyols, there are a wide variety of materials available which can be selected to give a wide spectrum of desired properties. In addition, the polyols have desirable reaction rates with polyisocyanates. Both saturated and unsaturated active hydrogen-containing compounds can be used, but saturated materials are particularly suitable because of superior coating properties.

The polyhydroxyl materials or polyols can be either low or high molecular weight materials and in general will have average hydroxyl values as determined by ASTM designation E-222-67, Method B, of 2000 and below, such as between 2000 and 10. The term "polyol" is meant to include materials having an average of two or more hydroxyl groups per molecule.

The polyols include low molecular weight diols, triols and higher molecular weight polyols, low molecular weight amide-containing polyols and higher polymeric polyols such as polyester polyols, polyether polyols, polycarbonate polyols and hydroxy-containing (meth)acrylic polymers. The polymers typically have hydroxyl values of from 10 to 180. Also, the polymers typically have number average molecular weights of 96 to 10,000 Da.

The low molecular weight diols, triols and higher alcohols useful in the instant invention are known in the art. They have hydroxy values of 200 or above, usually within the range of 200 to 2000. Such materials include aliphatic polyols, particularly alkylene polyols containing from 4 to 18 carbon atoms. Examples include 1,4-butanediol and 1,6-hexanediol. Also useful are polyols containing ether linkages such as diethylene glycol and tetraethylene glycol.

To form the polycarbodiimide, the polyisocyanate with or without the active hydrogen-containing compound may be condensed with the elimination of carbon dioxide to form the polycarbodiimide, that is, a polymer containing [N=C=N]$_n$ units where n with reference to the [N=C=N]=2 to 20, such as 2 to 10.

The condensation reaction is typically conducted by taking the solution of the polyisocyanate and heating in the presence of suitable catalyst. Examples of catalyst include 1-ethyl-3-phospholine, 1-ethyl-3-methyl-3-phospholine-1-oxide, 1-ethyl-3-methyl-3-phospholine-1-sulfide, 1-ethyl-3-methyl-phospholidine, 1-ethyl-3-methyl-phospholidine-1-oxide, 3-methyl-1-phenyl-3-phospholine-1-oxide and bicyclic terpene alkyl or hydrocarbyl aryl phosphine oxide or camphene phenyl phosphine oxide.

The particular amount of catalyst used will depend to a large extent on the reactivity of the catalyst itself and the polyisocyanate being used. A concentration range of 0.05-5 parts of catalyst per 100 parts of adduct is generally suitable.

The resulting polycarbodiimide has terminal NCO groups that can then be reacted with an active hydrogen-containing hydrophilic compound.

The hydrophilic compound may be a polyether alcohol or polyether amine or mixtures thereof having a polyether backbone, typically based on ethylene oxide or mixed ethylene oxide and propylene and having a molecular weight greater than 500, such as at least 1000 on a number average basis. Typical alcohols and amines have the following structural formula:

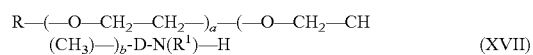

(XVII)

or

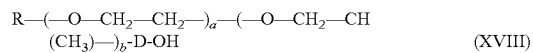

(XVIII)

where R with reference to formulas (XVII) and (XVIII) is $C_1$ to $C_4$ alkyl; a with reference to formulas (XVII) and (XVIII) is 5 to 50 and b with reference to formulas (XVII) and (XVIII) is 0 to 35, and when b with reference to formulas (XVII) and (XVIII) is present the mole ratio of a to b with reference to formulas (XVII) and (XVIII) is at least 1:1; $R^1$ with reference to formula (XVIII) is hydrogen or a hydrocarbon radical and D with reference to formulas (XVII) and (XVIII) is a divalent linking group or a chemical bond.

Reaction of the polyether alcohol or amine with the NCO-containing carbodiimide may be conducted with a stoichiometric equivalent of amine to NCO equivalents or a slight excess of alcohol or amine and at a temperature typically from 80 to 110° C. until an IR spectrum of the reaction mixture indicates substantially no remaining NCO functionality.

Depending on when the active hydrogen chain extender or spacer is used in the reaction, the polycarbodiimide has a structure such that each carbodiimide unit or polycarbodiimide unit is attached to a unit selected from urethane, thiourethane urea, thiourea and a hydrophilic unit occurs at one or terminal positions of the polycarbodiimide via a urethane or urea linkage.

Typically, the polycarbodiimide has a weight average molecular weight of 2600 to 12,000, such as 3000 to 10,000, and a diimide equivalent weight (number average molecular weight/number of carbodiimide groups) of at least 600, such as 600 to 2000.

When the active hydrogen chain extender is added before or during polycarbodiimide formation, that is, is used to chain extend a polyisocyanate to form an NCO-adduct, the polycarbodiimide can be represented from the following structural formula when the polyisocyanate and the active hydrogen-containing compound are difunctional:

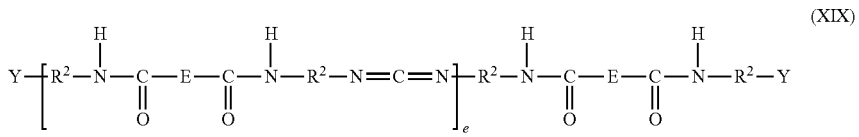
(XIX)

where e with reference to formula (XIX) is an integer of from 2 to 20, such as 2 to 10; E with reference to formula (XIX) is a radical selected from

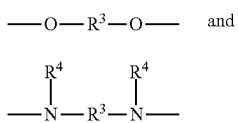

(XX)

(XXI)

where $R^2$ with reference to formula (XIX) is a cyclic radical such as a cycloaliphatic or an alkaryl radical that may contain 6 to 20 carbon atoms such as those of the structure:

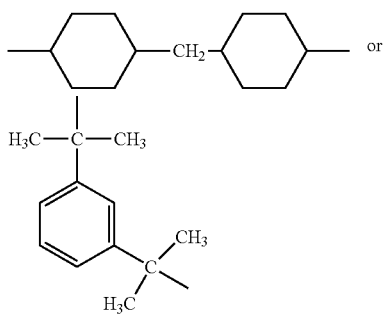

$R^3$ with reference to formula (XX) and (XXI) is a linear hydrocarbon radical optionally including hetero atoms containing at least 4 carbon atoms such as a polyethylene group having a number average molecular weight of 96 to 10,000. $R^4$ with reference to formula (XXI) is hydrogen or a hydrocarbon radical such as alkyl containing from 1 to 4 carbon atoms. Y with reference to formula (XIX) is a radical of the structure:

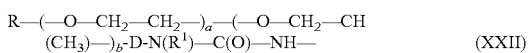
(XXII)

or

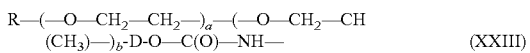
(XXIII)

where R with reference to formula (XXII) and (XXIII) is $C_1$ to $C_4$ alkyl; a with reference to formula (XXII) and (XXIII) is 5 to 50 and b with reference to formula (XXII) and (XXIII) is 0 to 35, and when b with reference to formulas (XXII) and (XXIII) is present the mole ratio of a to b with reference to formulas (XXII) and (XXIII) is at least 1:1; $R^1$ with reference to formula (XXII) is hydrogen or a hydrocarbon radical and D with reference to formula (XXII) and (XXIII) is a divalent linking group or a chemical bond.

When the active hydrogen chain extender is added after polycarbodiimide formation, that is, is used to chain extend an NCO-functional polycarbodiimide, the polycarbodiimide can be represented from the following structural formula when the NCO-functional polycarbodiimide and the active hydrogen-containing compound are difunctional.

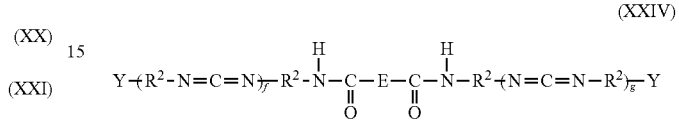
(XXIV)

where f and g with reference to formula (XXIV) are each at least 1, and f+g with reference to formula (XXIV) is an integer up to 20 such as up to 10; E with reference to formula (XXIV) is a radical selected from

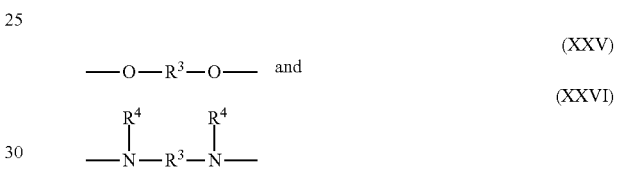

(XXV)

(XXVI)

where $R^2$, $R^3$, $R^4$ and Y with reference to formulas (XXIV), (XXV) and (XXVI) have the meanings mentioned above for (XIX).

Organic solvent can optionally be present in the synthesis of the polycarbodiimide. Polar water miscible solvents such as N-methyl pyrrolidone can be used in amounts of about 5-25 percent by weight based on weight of the reaction mixture.

The thermoset powder composition may comprise any suitable weight ratio of acid functional polyester material (a) to crosslinker (b). The thermoset powder may have a weight ratio of (a) to (b) from to 50:1 to 1:1, suitably from 25:1 to 1:1, such as from 20:1 to 5:1, or even from 15:1 to 5:1. Suitably, the thermoset powder may have a weight ratio of (a) to (b) of 10:1.

The thermoset powder of the present invention may have any suitable average particle size ($D_{50}$). The thermoset powder may have an average particle size from 5 to 300 microns (μm), suitably from 5 to 150 μm, such as from 10 to 75 μm, or even from 10 to 50 μm. Particles having these sizes may be produced by any suitable method. Suitable methods will be well known to a person skilled in the art. Examples of suitable methods include, but are not limited to, laser diffraction analysis, cold grinding and sieving methods.

Suitably, the average particle size ($D_{50}$) may be measured using laser diffraction analysis. The laser diffraction analysis may be performed using a Microtrac S3000 laser diffraction analyser (commercially available from Microtrac).

The coating composition of the present invention may comprise any suitable amount of acid functional polyester material. The coating composition may comprise from 1 to 100 wt %, suitably from 20 to 90 wt %, such as from 30 to 80 wt %, or even from 50 to 75 wt % of the polyester material based on the total solid weight of the coating composition.

The coating composition may comprise any suitable amount of crosslinker. The coating composition may comprise from 0.5 to 50 wt %, suitably from 1 to 40 wt %, such as from 2 to 30 wt %, or even from 5 to 20 wt % of the crosslinker based on the total solid weight of the coating composition. Suitably, the coating composition may comprise from 5 to 10 wt % of the crosslinker based on the total solid weight of the coating composition.

The coating composition may further comprise one or more pigment and/or filler. The coating composition may comprise a single pigment or filler or a mixture of pigments and/or fillers. Suitable pigments include, but are not limited to, the following: titanium dioxide; ultramarine blue; phthalocyanines, such as phthalocyanine blue and phthalocyanine green; anthraquinones; quinacridones; thioindigos; carbon black; graphite fibrils; iron oxides, such as black iron oxide; chromium green oxide; ferried yellow; quindo red; or combinations thereof. Suitable fillers include, but are not limited to, the following: barium sulphate; silicas, such as precipitated silicas and clay; or combinations thereof.

Suitably, the coating composition may comprise titanium dioxide, barium sulphate or a combination thereof. Suitably, the coating composition may comprise both titanium dioxide and barium sulphate.

The pigment and/or filler, when present, may be used in the coating composition in any suitable amount. The pigment and/or filler, when present, may be used in the coating composition in amounts of at least 10 wt % based on the total solid weight of the coating composition. The coating composition may comprise from 10 to 90 wt %, suitably from 10 to 80 wt %, such as from 10 to 70 wt %, or even from 10 to 50 wt % of pigment and/or filler based on the total solid weight of the coating composition. The coating composition may comprise from 15 to 90 wt %, suitably from 15 to 80 wt %, such as from 15 to 70 wt %, or even from 15 to 50 wt % of pigment and/or filler based on the total solid weight of the coating composition. The coating composition may comprise from 20 to 90 wt %, suitably from 20 to 80 wt %, such as from 20 to 70 wt %, or even from 20 to 50 wt % of pigment and/or filler based on the total solid weight of the coating composition.

The coating composition may further comprise one or more catalysts. The coating composition may comprise any catalyst suitable to catalyse the reaction between the acid functional polyester material and the β-hydroxyalkylamide crosslinker. Suitable catalysts will be well known to a person skilled in the art. Examples of suitable catalysts include, but are not limited to, the following: organic tin compounds, such as tin (II) salts of carboxylic acids, for example, tin (II) acetate, tin (II) octonoate, tin (II) ethylhexanoate and tin (II) laurate, tin (IV) compounds, for example, dibutyltin oxide, dibutyltin dichloride, dibutyltin diacetate, dibutyltin dilaurate, dibutyltin maleate and dioctyltin diacetate; tertiary amines, such as diazabicyclo[2.2.2]octane and 1,5-diazabicyclo[4.3.0]non-5-ene; and combinations thereof.

The coating compositions of the present invention may optionally comprise a further additive or combination of additives. Suitable additives will be well known to the person skilled in the art. Examples of suitable additives include, but are not limited to, the following: lubricants; diluents; plasticisers; surfactants; stabilising agents; flow control agents; thixotropic agents; and combinations thereof.

Suitable lubricants will be well known to the person skilled in the art. Suitable examples of lubricants include, but are not limited to one or more of the following: carnauba wax and polyethylene type lubricants. The lubricant, when present, may be used in the coating composition in amounts of at least 0.01 wt % based on the total solid weight of the coating composition.

Surfactants may optionally be added to the coating composition in order to aid in flow and wetting of the substrate. Suitable surfactants will be well known to the person skilled in the art. It will be appreciated by a person skilled in the art that when the coating composition is to be used in food and/or beverage container applications, the surfactant, when present, is chosen to be compatible with such applications. Suitable surfactants include, but are not limited to one or more of the following: alkyl sulphates (e.g., sodium lauryl sulphate); ether sulphates; phosphate esters; sulphonates; and their various alkali, ammonium, amine salts; aliphatic alcohol ethoxylates; alkyl phenol ethoxylates (e.g. nonyl phenol polyether); salts and/or combinations thereof. The surfactants, when present, may be present in amounts from about 0.01 to 10 wt % based on the total solid weight of the coating composition.

Suitable flow control agents will be well known to a person skilled in the art. Suitable flow control agents include, but are not limited to, the following: acrylate polymers, such as polylauryl acrylate, polybutyl acrylate, poly(2-ethylhexyl) acrylate, poly(ethyl-2-ethylhexyl) acrylate, polylauryl methacrylate and polyisodecenyl methacrylate; fluorinated polymers, such as an ester of polyethylene glycol or polypropylene glycol and fluorinated fatty acids, for example, an ester of polyethylene glycol of a molecular weight of over 2,500 Da and perfluorooctanoic acid; polymeric siloxanes, such as polymeric siloxanes of a molecular weight of over 1,000 Da, for example, poly(dimethylsiloxane) and poly(methylphenylsiloxane); and combinations thereof. The flow control agents, when present, may be present in amounts from 0.01 to 10 wt %, suitably from 0.1 to 5 wt %, such as from 0.5 to 4 wt %, or even from 1 to 3 wt % based on the total solid weight of the coating composition. It will be appreciated by a person skilled in the art that the flow controls agents, when present, should be suitable for use in a powder composition.

The coating compositions according to the present invention are substantially free of bisphenol A (BPA) and derivatives thereof. The coating compositions may be essentially free or may be completely free of bisphenol A (BPA) and derivatives thereof. Derivatives of bisphenol A include, for example, bisphenol A diglycidyl ether (BADGE). The coating compositions according to the present invention are also substantially free of bisphenol F (BPF) and derivatives thereof. The coating compositions may be essentially free or may be completely free of bisphenol F (BPF) and derivatives thereof. Derivatives of bisphenol F include, for example, bisphenol F diglycidyl ether (BPFG). The compounds or derivatives thereof mentioned above may not be added to the composition intentionally but may be present in trace amounts because of unavoidable contamination from the environment. "Substantially free" refers to coating compositions, or components thereof, containing less than 1000 parts per million (ppm) of any of the compounds or derivatives thereof mentioned above. "Essentially free" refers to coating compositions, or components thereof, containing less than 100 ppm of any of the compounds or derivatives thereof mentioned above. By "Completely free" refers to coating compositions, or components thereof, containing less than 20 parts per billion (ppb) of any of the compounds or derivatives thereof mentioned above.

The coating compositions of the present invention may be essentially fee or may be completely free of dialkyltin compounds, including oxides or other derivatives thereof.

Examples of dialkyltin compounds include, but are not limited to one or more of the following: dibutyltindilaurate (DBTDL); dioctyltindilaurate; dimethyltin oxide; diethyltin oxide; dipropyltin oxide; dibutyltin oxide (DBTO); dioctyltinoxide (DOTO) or combinations thereof. "Substantially free" refers to coating compositions, or components thereof, containing less than 1000 parts per million (ppm) of any of the compounds or derivatives thereof mentioned above. "Essentially free" refers to coating compositions, or components thereof, containing less than 100 ppm of any of the compounds or derivatives thereof mentioned above. "Completely free" refers to coating compositions, or components thereof, containing less than 0 parts per billion (ppb) of any of the compounds or derivatives thereof mentioned above.

The coating compositions of the present invention may be substantially free, may be essentially free or may be completely free of bromine "Substantially free" refers to coating compositions, or components thereof, containing less than 1000 parts per million (ppm) of any of the compounds or derivatives thereof mentioned above. "Essentially free" refers to coating compositions, or components thereof, containing less than 100 ppm of any of the compounds or derivatives thereof mentioned above. "Completely free" refers to coating compositions, or components thereof, containing less than 20 parts per billion (ppb) of any of the compounds or derivatives thereof mentioned above.

The coating compositions of the present invention may be substantially free, may be essentially free or may be completely free of solvent. "Substantially free" refers to coating compositions containing less than 1% of solvent. "Essentially free" refers to coating compositions containing less than 0.1% of solvent. "Completely free" refers to coating compositions containing less than 0.01% of solvent.

The thermoset powder composition of the present invention may be prepared by any suitable method. For example, the thermoset powder may be prepared by first dry blending an acid functional polyester material, an ß-hydroxyalkylamide crosslinker and, if present, pigment and/or filler, curing agent and additives in a blender. The blender may be operated for any suitable period of time. Suitably, the blender may be operated for a period of time sufficient to result in a homogeneous dry blend of the materials charged thereto. The homogenous dry blend may then be melt blended in an extruder, such as a twin-screw co-rotating extruder, operated within a temperature range from 80 to 140° C., suitably from 100 to 125° C. The extrudate of the thermoset powder may be cooled and milled to an average particle size as described above.

The coating composition of the present invention may be a curable coating composition. "Curable coating compositions" and like terms, as used herein, refers to coating compositions that have an initial powder state and a final state in which the coating composition has been transformed into a substantially continuous, coalesced state.

The coating composition of the present invention may be cured by any suitable method. The coating composition may be cured by heat curing or by chemical curing, suitably by heat curing. The coating composition, when heat cured, may be cured at any suitable temperature. The coating composition, when heat cured, may be cured at temperatures from 50 to 350° C., suitably from 100 to 320° C., such as from 150 to 300° C., or even from 200 to 300° C. Suitably, the coating composition, when heat cured, may be cured at 230° C. or at 250° C.

Curing the coating compositions of the present invention suitably forms a cured film. The cured film may have any suitable glass transition temperature (Tg). The cured film may have a Tg from 50 to 100° C., suitably from 60 to 100° C., such as from 70 to 90° C., or even from 75 to 90° C. Suitably, the cured film may have a Tg of at least 70° C., such as at least 75° C., or even at least 78° C. It has surprisingly and advantageously been found by the present inventors that when the Tg of the cured film is at least 78° C., the coatings compositions may be used on substrates that are to undergo a necking process, for example. It has surprisingly and advantageously been found by the present inventors that the cured film may have a Tg of at least 78° C. when the coating composition, when heat cured, is cured at a temperature of at least 250° C.

The Tg of the cured film may be measured by any suitable method. Methods to measure the Tg of the cured film will be well known to a person skilled in the art. Suitably, the Tg of the cured film is measured according to ASTM D6604-00 (2013) ("Standard Practice for Glass Transition Temperatures of Hydrocarbon Resins by Differential Scanning Calorimetry". Heat-flux differential scanning calorimetry (DSC), sample pans: aluminium, reference: blank, calibration: indium and mercury, sample weight: 10 mg, heating rate: 20° C./min). All values for Tg reported herein were measured in this way unless specified otherwise.

The coating composition according to the present invention are applied to at least a portion of an internal surface of a monobloc aerosol tube and/or can. Suitable examples of monobloc aerosol cans include, but are not limited to, deodorant and hair spray containers. Monobloc aerosol cans and/or tubes may be aluminium monobloc aerosol cans and/or tubes.

It has surprisingly and advantageously been found by the present inventors that the coating compositions of the present invention may be used as coatings for the internal surfaces of monobloc aerosol tubes or cans. Typically, the contents of monobloc aerosol tubes or cans are alkaline. It has surprisingly and advantageously been found by the present inventors that the coating compositions of the present invention are able to withstand contact with such alkaline chemicals. This is compared to, for example, food and/or beverage cans wherein the contents are typically acidic.

Therefore according to a further aspect of the present invention there is provided a monobloc aerosol tube or can being coated on at least a portion of an internal surface thereof with a coating composition, the coating composition comprising a thermoset powder composition; wherein the thermoset powder composition comprises an acid functional polyester material and a crosslinker material operable to crosslink the acid functionality on the acid functional polyester material; and wherein the coating composition is substantially free of bisphenol A (BPA), bisphenol F (BPF), bisphenol A diglycidyl ether (BADGE) and bisphenol F diglycidyl ether (BFDGE), wherein the monobloc aerosol tube or can contains an alkali material.

The coating compositions according to the present invention may be applied to the monobloc aerosol tube or can by any suitable method. Methods of applying said coating compositions to the monobloc aerosol tube or can will be well known to a person skilled in the art. Suitable application methods include, but are not limited to one or more of the following: spray coating; roll coating; dipping; and electrocoating such as, for example, ultra corona discharge. Suitably, the coating compositions according to the present invention may be applied to the monobloc aerosol can by ultra corona discharge.

When the substrate is electrically conductive, the coating composition is typically electrostatically applied. Electrostatic spray application generally involves drawing the coating composition from a fluidized bed and propelling it through a corona field. The particles of the coating composition become charged as they pass through the corona field and are attracted to and deposited upon the electrically conductive substrate, which is grounded. As the charged particles begin to build up, the substrate becomes insulated, thus limiting further particle deposition. This insulating phenomenon typically limits the film build of the deposited coating composition to a maximum of 250 to 300 μm (microns), in some cases, 75 to 150 μm.

The coating compositions according to the present invention may be applied to the monobloc aerosol tube or can to any suitable dry film thickness. The coating compositions according to the present invention may be applied to the monobloc aerosol tube or can to a dry film thickness from 0.1 μm (microns) to 300 μm, suitably from 3 μm to 250 μm, such as from 5 μm to 150 μm, or even from 5 μm to 75 μm, such as from 10 μm to 25 μm.

The coating composition according to the present invention may be applied to the monobloc aerosol can as a single layer or as part of a multi layer system. The coating compositions according to the present invention may be applied to the monobloc aerosol can as a single layer. The coating compositions according to the present invention may be applied to the monobloc aerosol can as the first coat of a multi coat system. Suitably, the coating composition according to the present may be applied to the monobloc aerosol can as an undercoat or a primer. The second, third, fourth etc. coats may comprise any suitable paint such as those containing, for example, epoxy resins; polyester resins; polyurethane resins; polysiloxane resins; hydrocarbon resins or combinations thereof. The coating compositions according to the present invention may be applied on top of another paint layer as part of a multi layer system. For example, the coating compositions according to the present invention may be applied on top of a primer. The coating compositions according to the present invention may form an intermediate layer or a top coat layer. The coating compositions according to the present invention may be applied to the monobloc aerosol can once or multiple times. Any or all of the layers may be substantially free, essentially free or completely free of BPA, BPF and derivatives thereof.

The acid functional polyester material of the present invention may have a glass transition temperature (Tg) from 50 to 100° C. and a viscosity from 10 to 50 Poise at 200° C.

According to a further aspect of the present invention there is provided a method of providing a monobloc aerosol tube or can internal having a coating composition on at least a portion thereof, the method comprising applying by ultra corona discharge a thermoset powder coating composition to a metal substrate; wherein the thermoset powder composition comprises an acid functional polyester material and a crosslinker material operable to crosslink the acid functionality on the acid functional polyester material; and wherein the coating composition is substantially free of bisphenol A (BPA), bisphenol F (BPF), bisphenol A diglycidyl ether (BADGE) and bisphenol F diglycidyl ether (BFDGE).

According to a further aspect of the present invention there is provided a monobloc aerosol tube or can being coated on at least a portion of an internal surface thereof with a coating composition, the coating composition comprising a thermoset powder composition, wherein the coating composition is substantially free of bisphenol A (BPA), bisphenol F (BPF), bisphenol A diglycidyl ether (BADGE) and bisphenol F diglycidyl ether (BFDGE).

According to a further aspect of the present invention there is provided a method of providing a monobloc aerosol tube or can internal having a coating composition on at least a portion thereof, the method comprising applying by ultra corona discharge a thermoset powder coating composition to a metal substrate, wherein the coating composition is substantially free of bisphenol A (BPA), bisphenol F (BPF), bisphenol A diglycidyl ether (BADGE) and bisphenol F diglycidyl ether (BFDGE).

According to a further aspect of the present invention there is provided a monobloc aerosol tube or can being coated on at least a portion of an internal surface thereof with a coating composition, the coating composition comprising a thermoset powder composition, wherein the coating composition is substantially free of bisphenol A (BPA), bisphenol F (BPF), bisphenol A diglycidyl ether (BADGE) and bisphenol F diglycidyl ether (BFDGE), wherein the monobloc aerosol tube or can contains an alkali material.

As used herein, unless otherwise expressly specified, all numbers such as those expressing values, ranges, amounts or percentages may be read as if prefaced by the word "about", even if the term does not expressly appear. Also, any numerical range recited herein is intended to include all sub-ranges subsumed therein. Singular encompasses plural and vice versa. For example, although reference is made herein to "a" hydroxy functional alkyl polyurea, "a" film forming resin, "an" isocyanate, "an" alkanol amine, "the" residue of "an", and the like, one or more of each of these and any other components can be used. As used herein, the term "polymer" refers to oligomers and both homopolymers and copolymers, and the prefix "poly" refers to two or more. Including, for example and like terms means including for example but not limited to.

All of the features contained herein may be combined with any of the above aspects and in any combination.

For a better understanding of the invention, and to show how embodiments of the same may be carried into effect, reference will now be made, by way of example, to the following experimental data.

EXAMPLES

Acid Functional Polyester Example 1

A polyester was prepared from the following ingredients using the following method: A total of 2,000 g neopentyl glycol, 640 g ethyl glycol, 4,330 g terephthalic acid, 260 g isophthalic acid and 6 g monobutyltin oxide were added to a reaction vessel equipped with a stirrer, temperature probe glycol recovery setup (a packed column and a distillation head connected to a water cooled condenser) and a nitrogen sparge. The contents of the reaction vessel were heated to 235° C. with continuous removal of water distillate beginning at 170° C. The contents of the reaction vessel were held at 235° C. until 760 g of water had been distilled and the acid value of the reaction mixture was found to be 20 mg KOH/g. A sample from the reaction vessel was checked for net hydroxyl value and was found to be 26.6 mg KOH/g.

Then, the contents of the reaction vessel were cooled to 190° C. and 770 g trimellitic anhydride was added to the reaction mixture. The contents of the reactor were held at 190° C. until 25 g water had been distilled and the acid value of the reaction mixture was found to be 80 mg KOH/g. The contents of the reaction vessel were kept at 190° C. and vacuum was applied until the acid value of the reaction mixture was found to be 73 mg KOH/g. The viscosity of the reaction mixture at this stage was 345 poise at 165° C.

The contents of the reaction vessel were kept at 190° C. before being poured out, cooled to room temperature and broken into chips. The reaction product has a measured solid content of 100%, an acid value of 72 mg KOH/g, a melt viscosity of 403 poise at 165° C., a net hydroxyl value- (minus) 68 mg KOH/g and a weight average molecular weight of 7,000 Da as measured against a polystyrene standard.

Acid Functional Polyester Example 2

An acid functional polyester was prepared from the following ingredients using the following method: A total of 5,892 g neopentyl glycol, 6,293 g terephthalic acid, 1,182 g isophthalic acid 3.1 g butylstannoic acid and 6.2 g of tris(nonylphenyl)phosphite were added to a reaction vessel equipped with a stirrer, temperature probe, a glycol recovery setup (a packed column and a distillation head connected to a water cooled condenser) and a nitrogen sparge. The contents of the reactor were heated to 235° C. with continuous removal of water distillate beginning at 140° C. The contents of the reactor were held at 235° C. until 1,620 g of water had been distilled and the acid number of the reaction mixture was found to be 14 mg KOH/g.

Then the contents of the reactor were cooled to 200° C. and 1,872 g isophthalic acid was added to the reaction mixture. The contents of the reactor were then heated to 235° C. and water was allowed to distill. The reactor was held at this temperature until 405 g of water had been distilled and the acid number of the reaction mixture was found to be 37 mg KOH/g.

Then the reaction mixture was cooled to 220° C. before 481 g of adipic acid was added to the reactor. The reactor was held at a temperature of 220° C. and water was allowed to distill. The contents of the reactor were held at this temperature until 118 g of water had been distilled and the acid number of the reaction mixture was found to be 46 mg KOH/g. After this, the contents of the reactor were held at 220° C. and a vacuum was applied to remove any remaining water. The vacuum was applied until the acid number of the reaction mixture was found to be 35 mg KOH/g. The reaction mixture was held at 190° C. before being discharged from the reactor.

The resulting polyester product has a measured solid content of 100%, an acid value of 35 mg KOH/g and a weight average molecular weight of 8,000 Da, as measured against a polystyrene standard.

Coating Compositions 1 and 2

Coating compositions 1, and 2 were prepared according to the formulations in Table 2. All amounts are given in parts by weight (pbw).

Comparative Coating Composition 1

Comparative coating composition 1 is a BPA-containing epoxy-based thermoset powder system available from TIGER Coatings GmbH & Co. KG and is a standard epoxy powder coating.

TABLE 2

Coating Composition Examples 1 and 2

|  | Coating composition 1 | Coating Composition 2 |
|---|---|---|
| Polyester example 1 | 67.48 | — |
| Polyester example 2 | — | 70.52 |
| β-hydroxyalkylamide crosslinker[1] | 7.29 | 4.25 |
| Pigment[2] | 9.45 | 9.86 |
| Filler[3] | 13.50 | 14.12 |
| Additive 1[4] | 1.08 | — |
| Additive 2[5] | 1.20 | 1.25 |
| PAdditive 3[6] | 0.3 | 0.3 |
| Total | 100.3 | 100.3 |

[1]PRIMID XL 552 available from Rohm and Haas
[2]TiONA 595 a titanium dioxide pigment available from CRISTAL
[3]Baramite Cimbar UF a barium sulphate filler available from CIMBAR Performance Minerals
[4]Resiflow PL 200 a flow agent available from Estron Chemical
[5]BYK-366P available from BYK-Chemie
[6]Aerosil 200 available from Evonik The properties of the coatings were tested via the following methods. Results are shown in Table 3.

Test Methods

Test Panel Preparation:

The coating samples were applied onto aluminium monobloc cans. Coating compositions 1 and 2 and comparative coating composition 1 were filled individually into an aluminium can and then drained for 10 minutes by standing the can upside down with an angle of 45°; thereby coating the internal of the can. Subsequently, the can was placed in a convection oven to be cured for 4 minutes at 230° C.

The coated cans were tested for coating thickness, enamel rating after the impact test, also known as the falling weight test, cross hatch adhesion, cross cut adhesion, blush, discolouration, scratch resistance, crazing after folding and adhesion after folding after exposure to boiling water and after exposure to deodorant, styling mousse or shaving foam according to the procedures described below.

Coating Thickness:

Coating thickness was measured according to a non-destructive measurement of anodic coatings applied onto an aluminium base, using an ISOSCOPE MP30, coating thickness measuring instrument. The uncoated aluminium can was used for calibration after it had been flattened. The thickness of the coating of the coated cans was measured both on the side wall and on the bottom of the can. The measured thickness was reported in microns and represented either the average of 10 measurements or the lowest and highest values.

Impact Test:

The impact test was carried out according to ASTM D2794. The bottom part of the coated can was cut at a height of 20 mm and then with the coated side facing down on a Teflon coated fixture. A 1 kg weight is dropped from a 1 meter height to strike an indentation. The test was repeated two times under the same conditions on two individual cans. The integrity of the coating was measured using a WACO Enamel Rater Instrument and a 1% salt solution containing 0.1% dioctyl sodium sulfosuccinate and reported in milliamperes (mA).

MEK Rub Test:

The number of reciprocating rubs required to remove the coating was measured using a ball of cotton wool soaked in methyl ethyl ketone (MEK).

Boiling Water Tests:

The coated parts of the can were immersed in boiling demineralised water at 100° C. fro 15 minutes and subsequently removed and dried. They were then tested for cross cut adhesion, cutting edge adhesion, resistance to blush and discolouration.

Cross cut adhesion was measured according to the DIN ISO 2409 standard. Briefly, a crosshatch grid was made in the film using a grid comb and was then covered with tape (grade TESA 4104 clear). Within 60 seconds of its application, the tape was removed rapidly. The grid area is then checked for removal of the coating from the substrate. The adhesion was scored in accordance with the following scale:

0: The edges of the cuts are completely smooth; none of the squares of the grid are detached.
1: Small flakes of the coating are detached at intersections; less than 5% of the area is affected.
2: Some flakes of the coating are detached along the edges and/or at intersections of the incisions. The area affected is 5-15% of the grid.
3: The coating has peeled along the edges and on parts of the squares of the grid. The area affected is 15-35% of the grid.
4: The coating has peeled along the edges of the incisions in large strips and some squares are totally detached. The area affected is 35-65% of the grid.
5: All degrees of peeling and flecking that can be not classified under 4.

Cutting edge adhesion was measured by the following method. The coated parts of the can were cut along the length of the can from the lowest film thickness to the highest film thickness using scissors. The cutting edge adhesion was evaluated according to the level of peeling from the substrate and using a rating of 1-5, with 5 being the best.

Resistance to blush, which is white colouration of the film caused by water penetration and entrapment was measured by the following method. The coated parts of the can are sterilised in an autoclave for 1 hour at 130° C. in a 1% solution of arylsulphosuccinate detergent in water and then the film is observed visually. The appearance of the film is rated between 0 and 5. Grade 0 corresponds to perfect film appearance with no discernible attack. Grade 5 corresponds to complete attack of the film across the whole of the score line.

Discolouration was measured by the following method. The coating is applied on can parts which are pre-coated with white enamel and sterilized in water with 1% teepol (sodium dodecyl benzene sulphonate detergent) for 1 hour at 130° C. and then the film is observed visually. The appearance is rated between 0 and 5. Grade 0 corresponds to no yellowing and grade 5 to a high yellowing level.

Pack Performance Tests:

Coated cans were packed with one of deodorant, styling mousse or shaving foam and left at 55° C. for two weeks. After this time, the cans were then tested for cross cut adhesion, cutting edge adhesion, blush, discolouration, scratch resistance, crazing after folding and adhesion after folding according to the same methods as described above in relation to the boiling water tests.

TABLE 2

Test Results

| | Coating Composition 1 | Coating Composition 2 | Comparative Coating Composition 1 |
|---|---|---|---|
| Flexibility | | | |
| Thickness/μm - A | 37-41 | 29-31 | 28-30 |
| Thickness/μm - B | 12-16 | 37-43 | 19-23 |
| Enamel rater/mA - A | 4.8 | 0.4 | 0 |
| Enamel rater/mA - B | 0.3 | 0 | 0.5 |
| MEK Resistance | | | |
| Thickness/μm - A | 16-27 | 16-25 | 14-25 |
| Thickness/μm - B | 15-27 | 18-24 | 15-29 |
| MEK double rubs - A | 100 | 48 | 100 |
| MEK double rubs - B | 100 | 40 | 100 |
| Boiling Tests (15 mins @ 100° C. in demineralised water) | | | |
| Thickness/μm - A | 16-26 | 17-32 | 16-37 |
| Thickness/μm - B | 15-27 | 16-24 | 14-25 |
| Cross hatch adhesion - A | 0 | 0 | 0.5 |
| Cross hatch adhesion - B | 0 | 0 | 0 |
| Cutting edge adhesion - A | 5 | 5 | 5 |
| Cutting edge adhesion - B | 5 | 5 | 4.5 |
| Blush - A | 5 | 5 | 5 |
| Blush - B | 5 | 5 | 5 |
| Discolouration - A | 4 | 4 | 4* |
| Discolouration - B | 4 | 4 | 4* |
| Pack Performance after 2 weeks at 55° C. Deodorant | | | |
| Thickness/μm - A | 18-21 | 9-21 | 23-25 |
| Thickness/μm - B | 21-23 | 10-28 | 20-25 |
| Cross hatch adhesion - A | 5 | 5 | 5 |
| Cross hatch adhesion - B | 5 | 5 | 5 |
| Cutting edge adhesion - A | 5 | 5 | 5 |
| Cutting edge adhesion - B | 5 | 5 | 5 |
| Blush - A | 3.5* | 5 | 2 |
| Blush - B | 3* | 5 | 2 |
| Discolouration - A | 5 | 5 | 5 |
| Discolouration - B | 5 | 5 | 5 |
| Styling Mousse | | | |
| Thickness/μm - A | 19-22 | 7-20 | 21-30 |
| Thickness/μm - B | 20-22 | 12-26 | 17-25 |
| Cross hatch adhesion - A | 5 | 5 | 5 |
| Cross hatch adhesion - B | 5 | 5 | 5 |
| Cutting edge adhesion - A | 5 | 4 | 5 |
| Cutting edge adhesion - B | 5 | 4 | 5 |
| Blush - A | 4.5 | 5 | 4.5 |
| Blush - B | 4.5* | 5 | 5 |
| Discolouration - A | 5 | 5 | 5 |
| Discolouration - B | 5 | 4.5 | 5 |
| Shaving Foam | | | |
| Thickness/μm - A | 19-26 | 5-16 | 12-34 |
| Thickness/μm - B | 22-23 | 9-30 | 17-26 |
| Cross hatch adhesion - A | 4.5 | complete | 5 |
| Cross hatch adhesion - B | 5 | delamination | 5 |
| Cutting edge adhesion - A | 4.5 | | 5 |
| Cutting edge adhesion - B | 4.5 | | 5 |
| Blush - A | 4 | | 4 |
| Blush - B | 4 | | 4 |
| Discolouration - A | 4 | | 5 |
| Discolouration - B | 4.5 | | 5 |

The results show that the coating compositions according to the present invention perform as well, or better, than the liquid coatings of the comparative examples.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A monobloc aerosol tube or can coated on at least a portion of an internal surface thereof with a coating composition, the coating composition comprising a thermoset powder composition, wherein the coating composition is substantially free of bisphenol A (BPA), bisphenol F (BPF), bisphenol A diglycidyl ether (BADGE) and bisphenol F diglycidyl ether (BFDGE); and wherein the thermoset powder composition comprises an acid functional polyester material having an acid number (AN) of 30 mg KOH/g to 100 mg KOH/g and a crosslinker material operable to crosslink the acid functionality on the acid functional polyester material.

2. The monobloc aerosol tube or can according to claim 1, wherein the acid functional polyester material has a gross OHV up to 5.0 mg KOH/g.

3. The monobloc aerosol tube or can according to claim 1, wherein the acid functional polyester material has a Tg from 60° C. to 70° C.

4. The monobloc aerosol tube or can according to claim 1, wherein the acid functional polyester material has a viscosity at 200° C. from 2 to 100 Poise.

5. The monobloc aerosol tube or can according to claim 1, wherein the crosslinker material comprises a hydroxyalkylamide material and/or a hydroxyalkylurea material and/or a carbodiimide resin.

6. The monobloc aerosol tube or can according to claim 1, wherein the crosslinker material comprises a terminal chemical group as shown in Formula IV:

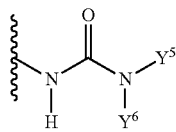

Formula IV wherein $Y^5$ and $Y^6$ each, independently, represent hydrogen, an alkyl or a hydroxy functional alkyl having two or more carbon atoms and at least one of $Y^5$ and $Y^6$ is a hydroxyl functional alkyl having two or more carbon atoms.

7. The monobloc aerosol tube or can according to claim 1, wherein the acid functional polyester material has a glass transition temperature (Tg) from 50 to 100° C. and a viscosity from 10 to 50 Poise.

8. The monobloc aerosol tube or can according to claim 1, wherein a weight ratio of the acid functional polyester material to crosslinker material is from 50:1 to 1:1.

9. The monobloc aerosol tube or can according to claim 1, wherein the thermoset powder composition has an average particle size ($D_{50}$) from 5 to 300 microns (μm) as measured using laser diffraction analysis.

10. The monobloc aerosol tube or can according to claim 1, wherein the acid functional polyester material comprises the reaction product of a polyacid and a polyol.

11. The monobloc aerosol tube or can according to claim 10, wherein the polyacid comprises at least 50 mol % terephthalic acid and/or isophthalic acid based on the total number of moles of polyacid.

12. The monobloc aerosol tube or can according to claim 10, wherein the polyol comprises at least 10 mol % of neopentyl glycol based on the total number of moles of polyol.

13. The monobloc aerosol tube or can according to claim 10, wherein a molar ratio of the polyacid to the polyol in the acid functional polyester material is from 20:1 to 1:20.

14. The monobloc aerosol tube or can according to claim 5, wherein the crosslinker material contains a terminal chemical group as shown in Formula I:

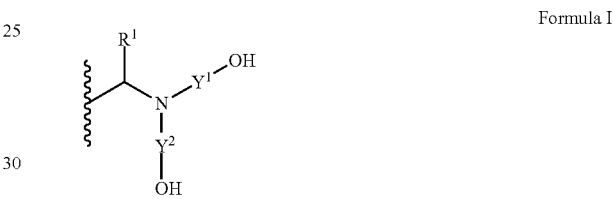

Formula I wherein $R^1$ represents an electron withdrawing group, such as (=O); and $Y^1$ and $Y^2$ each, independently, represents a $C_1$ to $C_3$ alkylene group.

15. The monobloc aerosol tube or can according to claim 5, wherein the crosslinker material comprises a moiety according to Formula II:

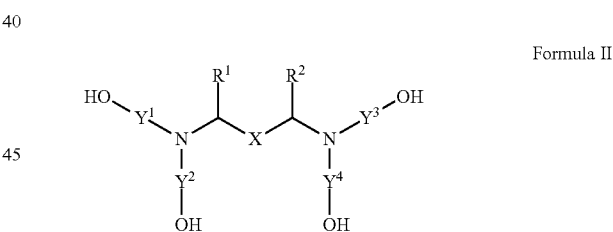

Formula II wherein $R^1$ and $R^2$ each, independently, represent an electron withdrawing group, such as (=O); $Y^1$, $Y^2$, $Y^3$ and $Y^4$ each, independently, represent a $C_1$ to $C_3$ alkylene group; and X is a C2 to C6 alkylene group.

16. A monobloc aerosol tube or can coated on at least a portion of an internal surface thereof with a coating derived from a coating composition comprising a thermoset powder composition, wherein the coating composition is substantially free of bisphenol A (BPA), bisphenol F (BPF), bisphenol A diglycidyl ether (BADGE) and bisphenol F diglycidyl ether (BFDGE), wherein the thermoset powder composition comprises an acid functional polyester material having an acid number (AN) of 30 mg KOH/g to 100 mg KOH/g and a crosslinker material operable to crosslink the acid functionality on the acid functional polyester material.

17. The monobloc aerosol tube or can according to claim 14, wherein the monobloc aerosol tube or can contains an alkali material disposed therein.

18. The monobloc aerosol tube or can according to claim 16, wherein the coating has a dry film thickness from 10 μm to 25 μm.

19. A method of coating a monobloc aerosol tube or can, the method comprising applying by ultra corona discharge a thermoset powder coating composition to a metal substrate of the monobloc aerosol tube or can, wherein the thermoset powder coating composition is substantially free of bisphenol A (BPA), bisphenol F (BPF), bisphenol A diglycidyl ether (BADGE) and bisphenol F diglycidyl ether (BFDGE); wherein the thermoset powder coating composition comprises an acid functional polyester material having an acid number (AN) of 30 mg KOH/g to 100 mg KOH/g and a crosslinker material operable to crosslink the acid functionality on the acid functional polyester material.

* * * * *